United States Patent [19]

Inoue et al.

[11] Patent Number: 5,977,023
[45] Date of Patent: *Nov. 2, 1999

[54] SUSTAINED RELEASE, SOLID PESTICIDAL COMPOSITIONS COMPRISING WATER INSOLUBLE ALGINATES

[75] Inventors: Masao Inoue, Hyogo-ken; Masao Ogawa, Osaka-fu; Toshiro Ohtsubo, Hyogo-ken, all of Japan

[73] Assignee: Sumitomo Chemical Company, Limited, Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/939,166

[22] Filed: Sep. 29, 1997

Related U.S. Application Data

[63] Continuation of application No. 08/318,106, Oct. 5, 1994, abandoned.

[30] Foreign Application Priority Data

| Oct. 5, 1993 | [JP] | Japan | 5-249489 |
| Oct. 6, 1993 | [JP] | Japan | 5-250601 |
| Oct. 15, 1993 | [JP] | Japan | 5-258557 |
| Dec. 20, 1993 | [JP] | Japan | 5-319596 |
| May 26, 1994 | [JP] | Japan | 6-112978 |

[51] Int. Cl.[6] .......................... A01N 25/10; A01N 25/12; A01N 25/26
[52] U.S. Cl. ........................... 504/116; 424/405
[58] Field of Search ............................. 504/116; 424/405

[56] References Cited

U.S. PATENT DOCUMENTS

| 4,400,391 | 8/1983 | Connick, Jr. | 424/304 |
| 4,401,456 | 8/1983 | Connick, Jr. | 424/304 |
| 5,009,710 | 4/1991 | Bewsey | 106/208 |

FOREIGN PATENT DOCUMENTS

| 1299378 | 12/1972 | United Kingdom . |
| 9101803 | 2/1991 | WIPO . |

OTHER PUBLICATIONS

Journal of Controlled Release, vol. 17, No. 1, Sep. 1991, Amsterdam NL, pp. 105–111.

A. Pepperman et al., "Slow release formulations of metribuzin based on alginate–kaolin–linseed oil", Journal of Controlled Release, 26, 1993, pp. 21–30.

A. Pepperman et al., "Alginate controlled release formulations of metribuzin", Journal of Controlled Release, 17, 1991, pp. 105–112.

*Primary Examiner*—S. Mark Clardy
*Attorney, Agent, or Firm*—Sughrue, Mion, Zinn, Macpeak & Seas, PLLC

[57] ABSTRACT

There are discolsed a pesticidal composition containing a water-insoluble alginate, which is prepared by treating a solid composition containing (a) a pesticidally active ingredient which is a pest-controlling active ingredient or a plant growth-regulating active ingredient and (b) an alginic acid or a water-soluble alginate with an aqueous solution containing a divalent or polyvalent cation which can convert said alginic acid or water-soluble alginate into a water-insoluble alginate. Also disclosed is a pesticidal composition containing a water-insoluble alginate, which is prepared by coating a solid substance containing the pesticidally active ingredient with a water-insoluble alginate. The composition of the invention has excellent sustained-release effects of the pesticidally active ingredient.

22 Claims, No Drawings

5,977,023

SUSTAINED RELEASE, SOLID PESTICIDAL COMPOSITIONS COMPRISING WATER INSOLUBLE ALGINATES

This is a Continuation of application Ser. No. 08/318,106 filed Oct. 5, 1994, abandoned.

FIELD OF THE INVENTION

The present invention relates to a pesticidal composition wherein release of a pesticidally active ingredient which is a pest-controlling active ingredient or a plant growth-regulating active ingredient, is effectively controlled. The invention also relates to a method for preparing such a pesticidal composition and use of the same.

BACKGROUND OF THE INVENTION

A variety of pesticides have been developed and used in many fields. Sustained release of a pesticidally active ingredient from a pesticidal composition into soil, water, or another specific environment allows sustainable effects of the pesticide on target pest and reduces the phytotoxicity of the composition on plants. Irrespective of wide researches and investigations, however, any method of realizing sufficient sustained release of a pesticidally active ingredient has not been found yet.

SUMMARY OF THE INVENTION

As a result of extensive study, the inventors have found that a certain pesticidal composition containing a water-insoluble alginate can control release of a pesticidally active ingredient contained in the pesticial composition, and has excellent sustained-release effects.

DETAILED DESCRIPTION OF THE INVENTION

The invention is directed to a pesticidal composition containing a water-insoluble alginate, which is prepared by treating a solid composition containing (a) a pesticidally active ingredient which is a pest-controlling active ingredient or a plant growth-regulating active ingredient and (b) an alginic acid or a water-soluble alginate with an aqueous solution containing a divalent or polyvalent cation which can convert said alginic acid or water-soluble alginate into a water-insoluble alginate.

The invention is also directed to a pesticidal composition containing a water-insoluble alginate, which is prepared by coating a solid substance containing a pesticidally active ingredient which is a pest-controlling active ingredient or a plant growth-regulating active ingredient with a water-insoluble alginate.

The pesticidal composition of the invention has excellent sustained-release effects of the pesticidally active ingredient. The composition of the invention is improved from the view point of the hardness. The composition of the invention can be prepared to any desirable shape and size according to its applications.

Typical examples of such compositions are a composition wherein the water-insoluble alginate has a three dimensional matrix structure (hereinafter referred to as Composition A), a composition wherein the solid substance containing the pesticidally active ingredient is coated with the water-insoluble alginate (hereinafter referred to as Composition B), and a composition wherein the water-insoluble alginate is impregnated into the solid substance containing the pesticidally active ingredient (hereinafter referred to as Composition C). The Composition A is especially preferable for continuous production.

The composition of the invention is prepared by treating a solid composition containing a pesticidally active ingredient which is a pest-controlling active ingredient or a plant growth-regulating active ingredient and an alginic acid or a water-soluble alginate with an aqueous solution containing a divalent or polyvalent cation which can convert the alginic acid or water-soluble alginate into a water-insoluble alginate. Otherwise, the composition of the invention is prepared by coating a solid substance containing a pesticidally active ingredient which is a pest-controlling active ingredient or a plant growth-regulating active ingredient with a water-insoluble alginate.

The pesticidally active ingredient contained in the composition of the invention may be a pest-controlling active ingredient such as active ingredient of any insecticide, acaricide, insect growth regulator, fungicide, herbicide, nematicide, and rodenticide, or a plant growth-regulating active ingredient. Typical examples of the pesticidally active ingredient include compounds listed below, active isomers thereof, and admixtures thereof. Preferable examples are those having relatively low water solubility, more specifically those having water solubility of not greater than 2,000 ppm at 20° C. Among them, those having water solubility of not greater than 500ppm at 20° C. are more preferable.

Examples of the pesticidally active ingredient are given below with reference numbers:

(1) α-cyano-3-phenoxybenzyl 2-(4-chlorophenyl)-3-methylbutyrate,
(2) (S)-α-cyano-3-phenoxybenzyl (S)-2-(4-chlorophenyl)-3-methylbutyrate,
(3) α-cyano-3-phenoxybenzyl 2,2,3,3-tetramethyl-cyclo propanecarboxylate,
(4) 3-phenoxybenzyl 3-(2,2-dichlorovinyl)-2,2-dimethyl cyclopropanecarboxylate,
(5) 3-phenoxybenzyl chrysanthemate,
(6) 3-phenoxybenzyl (1R)-chrysanthemate,
(7) α-cyano-3-phenoxybenzyl 3-(2,2-dichlorovinyl)-2,2-dimethylcyclopropanecarboxylate,
(8) α-cyano-3-(4-bromophenoxy)benzyl 3-(2,2-dichlorovinyl)-2,2-dimethylcyclopropanecarboxylate,
(9) α-cyano-3-(4-fluorophenoxy)benzyl 3-(2,2-dichlorovinyl)-2,2-dimethylcyclopropanecarboxylate,
(10) α-cyano-3-(3-bromophenoxy)benzyl 3-(2,2-dichlorovinyl)-2,2-dimethylcyclopropanecarboxylate,
(11) α-cyano-3-(4-chlorophenoxy)benzyl 3-(2,2-dichlorovinyl)-2,2-dimethylcyclopropanecarboxylate,
(12) α-cyano-3-phenoxybenzyl chrysanthemate,
(13) α-cyano-3-phenoxybenzyl (1R)-chrysanthemate,
(14) α-cyano-3-(4-bromophenoxy)benzyl 2-(4-chlorophenyl)-3-methylbutyrate,
(15) α-cyano-3-(3-bromophenoxy)benzyl 2-(4-chlorophenyl)-3-methylbutyrate,
(16) α-cyano-3-(4-chlorophenoxy)benzyl 2-(4-chlorophenyl)-3-methylbutyrate,
(17) α-cyano-3-(4-fluorophenoxy)benzyl 2-(4-chlorophenyl)-3-methylbutyrate,
(18) α-cyano-3-phenoxybenzyl 2-(4-bromophenyl)-3-methylbutyrate,
(19) α-cyano-3-phenoxybenzyl 2-(4-tert-butylphenyl)-3-methylbutyrate,
(20) α-cyano-3-phenoxybenzyl 2-(3,4-methylenedioxyphenyl)-3-methylbutyrate,
(21) α-cyano-4-fluoro-3-phenoxybenzyl 3-(2,2-dichlorovinyl)-2,2-dimethylcyclopropanecarboxylate,
(22) α-cyano-3-phenoxybenzyl 2-(2-chloro-4-trifluoromethylanilino)-3-methylbutyrate,

(23) α-cyano-3-phenoxybenzyl 2-(4-difluoromethoxyphenyl)-3-methylbutyrate,
(24) α-cyano-3-phenoxybenzyl (S)-2-(4-difluoromethoxyphenyl)-3-methylbutyrate,
(25) cyano-(5-phenoxy-2-pyridyl)methyl 3-(2,2-dichlorovinyl)-2,2-dimethylcyclopropanecarboxylate,
(26) α-cyano-3-phenoxybenzyl 2,2-dimethyl-3-(1,2,2,2-tetrabromoethyl)cyclopropanecarboxylate,
(27) α-cyano-3-phenoxybenzyl 2,2-dimethyl-3-(1,2-dichloro-2,2-dibromoethyl)cyclopropanecarboxylate,
(28) α-cyano-3-phenoxybenzyl 1-(4-ethoxyphenyl)-2,2-dichlorocyclopropanecarboxylate,
(29) α-cyano-3-phenoxybenzyl 2,2-dimethyl-3-(2-chloro-2-trifluoromethylvinyl)cyclopropanecarboxylate,
(30) 2-(4-ethoxyphenyl)-2-methylpropyl 3-phenoxybenzyl ether,
(31) 2-(4-ethoxyphenyl)-3,3,3-trifluoropropyl 3-phenoxybenzyl ether,
(32) 2-methyl-3-phenylbenzyl (1R, trans)-2,2-dimethyl-3-(2-chloro-2-trifluoromethylvinyl)cyclopropanecarboxylate,
(33) 2,3,5,6-tetrafluoro-4-methylbenzyl (1R, trans)-2,2-dimethyl-3-(2-chloro-2-trifluoromethylvinyl)cyclopropanecarboxylate,
(34) 3,4,5,6-tetrahydrophthalimidomethyl chrysanthemate,
(35) 3,4,5,6-tetrahydrophthalimidomethyl (1R)-chrysanthemate,
(36) 3-allyl-2-methyl-4-oxocyclopent-2-enyl chrysanthemate,
(37) 3-allyl-2-methyl-4-oxocyclopent-2-enyl (1R)-chrysanthemate,
(38) (S)-2-methyl-4-oxo-3-(2-propynyl)cyclopent-2-enyl (1R)-chrysanthemate,
(39) 1-ethynyl-2-methyl-2-pentenyl (1R)-chrysanthemate,
(40) 5-benzyl-3-furylmethyl chrysanthemate,
(41) 5-benzyl-3-furyrlmethyl (IR)-chrysanthemate,
(42) α-cyano-3-(4-bromophenoxy)benzyl 3-(2,2-dibromovinyl)-2,2-dimethylcyclopropanecarboxylate,
(43) 0,0-dimethyl 0-(3-methyl-4-nitrophenyl) phosphorothioate,
(44) 0,0-dimethyl S-[1,2-di(ethoxycarbonyl)ethyl] phosphorodithioate,
(45) 0,0-dimethyl 0-(4-cyanophenyl) phosphorothioate,
(46) 0,0-dimethyl S-(α-ethoxylcarbonylbenzyl) phosphorodithioate,
(47) 0,0-diethyl 0-(2-isopropyl-4-methyl-6-pyrimidinyl) phosphorothioate,
(48) 0,0-dimethyl 0-[3-methyl-4-(methylthio)phenyl] phosphorothioate,
(49) 0-(4-bromo-2,5-dichlorophenyl) 0.0-diethylphosphorothioate,
(50) 2-methoxy-4H-1,3,2-benzoxaphosphorin-2-sulfide,
(51) 0,0-dimethyl 0-(2,4,5-trichlorophenyl) phosphorothioate,
(52) 0,0-diethyl 0-(3,5,6-trichloro-2-pyridyl) phosphorothioate,
(53) 0,0-dimethyl 0-(3,5,6-trichloro-2-pyridyl) phosphorothioate,
(54) 0,0-dimethyl 0-(4-bromo-2,5-dichlorophenyl) phosphorothioate,
(55) 0-(2,4-dichlorophenyl) 0-ethyl S-propyl phosphorodithioate,
(56) 0,0-dimethyl S-(5-methoxy-1,3,4-thiadiazolin-2-on-3-ylmethyl) phosphorodithioate,
(57) dimethyl 2,2,2-trichloro-l-hydroxyethylphosphonate,
(58) 0-ethyl 0-(4-nitrophenyl)benzenephosphonothioate,
(59) 0,0-dimethyl S-(N-methylcarbamoylmethyl) phosphorodithioate,
(60) 2-sec-butylphenyl N-methylcarbamate,
(61) 3-methylphenyl N-methylcarbamate,
(62) 3,4-dimethylphenyl N-methylcarbamate,
(63) 2-isopropoxyphenyl N-methylcarbamate,
(64) 1-naphthyl N-methylcarbamate,
(65) 2-isopropylphenyl N-methylcarbamate,
(66) 0,0-diethyl S-[2-(ethylthio)ethyl]phosphorodithioate,
(67) trans-5-(4-chlorophenyl)-N-cyclohexyl-4-methyl-2-oxothiazolidin-3-carboxyamide,
(68) 2,3-dihydro-2,2-dimethyl-7-benzofuranyl N-dibutylaminothio-N-methylcarbamate,
(69) ethyl N-[2,3-dihydro-2,2-dimethylbenzofuran-7-yloxycarbonyl(methyl)aminothio]-N-isopropyl-β-alaninate,
(70) 1-[3,5-dichloro-4-(3-chloro-5-trifluoromethyl-2-pyridyloxy) phenyl]-3-(2,6-difluorobenzoyl)urea,
(71) 1-(3,5-dichloro-2,4-difluoropheyl)-3-(2,6-difluorobenzoyl)urea,
(72) 1-[3,5-dichloro-4-(1,1,2,2-tetrafluoroethoxy)-phenyl]-3-(2,6-difluorobenzoyl)urea,
(73) ethyl 2-(4-phenoxyphenoxy)ethylcarbamate,
(74) 2-tert-butyl-5-(4-tert-butylbenzylthio)-4-chloropyridazin-3(2H)-one,
(75) 1-[4-(2-chloro-4-trifluoromethylphenoxy)-2-fluorophenyl]-3-(2,6-difluorobenzoyl)urea,
(76) tert-butyl (E)-α-(1,3-dimethyl-5-phenoxypyrazol-4-ylmethyleneaminoxy)-p-toluate,
(77) 3,7,9,13-tetramethyl-5,11-dioxa-2,8,14-trithia-4,7,9,12-tetraazapentadeca-3,12-diene-6,10-dione,
(78) 1-(6-chloro-3-pyridylmethyl)-N-nitroimidazolidin-2-ylidenamine,
(79) 5-ethoxy-3-trichloromethyl-1,2,4-thiadiazole,
(80) 0,0-diisopropyl S-benzyl phosphorothiolate,
(81) 0-ethyl S,S-diphenyl dithiophosphate,
(82) 3,4-dichloropropionanilide,
(83) isopropyl N-(3-chlorophenyl)carbamate,
(84) S-ethyl N,N-dipropylthiolcarbamate,
(85) 3-methoxycarbonylaminophenyl N-(3-methyl-phenyl) carbamate,
(86) N-methoxymethyl-2-chloro-2',6'-diethylacetanilide,
(87) 2,6-dinitro-N,N-dipropyl-4-trifluoromethylaniline,
(88) S-(4-chlorobenzyl) N,N-diethylthiolcarbamate,
(89) S-ethyl N,N-hexamethylenethiolcarbamate,
(90) N-(1,1,3-trimethyl-2-oxa-4-indanyl)-5-chloro-1,3-dimethylpyrazol-4-carboxamide,
(91) 3'-isopropoxy-2-(trifluoromethyl)benzanilide,
(92) diisopropyl 1,3-dithiolan-2-ilidenemalonate,
(93) 1,2,5,6-tetrahydropyrrolo[3,2,1-i,j]quinolin-4-one,
(94) 3-allyloxy-1,2-benzoisothiazole-1,1-dioxide,
(95) 5-methyl[1,2,4]triazolo[3,4-b]benzothiazole,
(96) 1,2-bis(3-methoxycarbonyl-2-thioureido)benzene,
(97) 1-(4-chlorobenzyl)-1-cyclopentyl-3-phenylurea,
(98) 6-(3,5-dichloro-4-methylphenyl)-3(2H)-pyridazinone,
(99) methyl 1-(butylcarbamoyl)benzimidazole-2-carbamate,
(100) 3-(3,5-dichlorophenyl)-N-isopropyl-2,4-dioxoimidazolidine-1-carboxamide,
(101) 3-(3,5-dichlorophenyl)-5-methyl-5-vinyl-1,3-oxazolidine-2,4-dione,
(102) manganese ethylenebisdithiocarbamate,
(103) manganese and zinc ethylenebisdithiocarbamate,
(104) N-(trichloromethylthio)cyclohex-4-en-1,2-dicarboximide,
(105) 3'-isopropoxy-2-methylbenzanilide,
(106) tetrachloroisophthalonitrile,
(107) 1-(4-chlorophenoxy)-3,3-dimethyl-1-(1H-1,2,4-triazol-1-yl)butanone,
(108) (E)-4-chloro-2-(trifluoromethyl)-N-[1-imidazol-1-yl)-2-propoxyethylidene]aniline, (109) methyl N-(methoxyacetyl)-N-(2,6-dimethyl-phenyl) alaninate,
(110) 3-chloro-N-(3-chloro-5-trifluoromethyl-2-pyridyl)-2,6-dinitro-4-methylaniline,
(111) N-butoxymethyl-2-chloro-2',6'-diethylacetanilide,
(112) O-ethyl O-(5-methyl-2-nitrophenyl)-sec-butyl phosphoroamidethioate,
(113) ethyl N-chloroacetyl-N-(2,6-diethylphenyl)glycinate
(114) 2-[1-methyl-2-(4-phenoxyphenoxy)ethoxy]pyridine
(115) (E)-1-(4-chlorophenyl)-4,4-dimethyl-2-(1H-1,2,4-triazol-1-yl)-1-penten-3-ol,
(116) 1-(4-chlorophenyl)-4,4-dimethyl-2-(1H-1,2,4-triazol-1-yl)pentan-3-ol,
(117) 2-bromo-N-(α,α-dimethylbenzyl)-3,3-dimethylbutanamide,
(118) 1-(1-methyl-1-phenylethyl)-3-(p-tolyl)urea,
(119) 2-(2-naphthoxy)propionanilide,
(120) 2-(2,4-dichloro-3-methylphenoxy)propionanilide,
(121) 4-(2,4-dichlorobenzoyl)-1,3-dimethyl-5-pyrazolyl p-toluenesulfonate,
(122) 4-(2,4-dichlorobenzoyl)-1,3-dimethyl-5-phenacyloxypyrazole,
(123) 4-(2,4-dichloro-3-methylbenzoyl)-1,3-dimethyl-5-(4-methylphenacyloxy)pyrazole,
(124) 2,4,6-trichlorophenyl 4-nitrophenyl ether,
(125) 2,4-dichlorophenyl 3-methoxy-4-nitrophenyl ether,
(126) 2,4-dichlorophenyl 3-methoxycarbonyl-4-nitrophenyl ether,
(127) 2-benzothiazol-2-yloxy-N-methylacetanilide,
(128) 2',3'-dichloro-4-ethoxymethoxybenzanilide,
(129) 5-tert-butyl-3-(2,4-dichloro-5-isopropoxyphenyl)-1,3,4-oxadiazol-2(3H)-one,
(130) 2-amino-3-chloro-1,4-naphthoquinone,
(131) methyl 2-[3-(4,6-dimethoxypyrimidin-2-yl)-ureidosulfonylmethyl]benzoate,
(133) ethyl 5-[3-(4,6-dimethoxypyrimidin-2-yl)-ureidosulfonyl]-1-methylpyrazole-4-carboxylate,
(134) 3-chloro-2-[4-chloro-2-fluoro-5-(2-propynyloxy)-phenyl]-4,5,6,7-tetrahydro-2H-indazole,
(135) O-(4-tert-butylphenyl) N-(6-methoxy-2-pyridyl)-N-methylthionocarbamate,
(136) O-(3-tert-butylphenyl) N-(6-methoxy-2-pyridyl)-N-methylthionocarbamate,
(137) O-(4-chloro-3-ethylphenyl) N-(6-methoxy-2-pyridyl)-N-methylthionocarbamate,
(138) O-(4-bromo-3-ethylphenyl) N-(6-methoxy-2-pyridyl)-N-methylthionocarbamate,
(139) O-(3-tert-butyl-4-chlorophenyl) N-(6-methoxy-2-pyridyl)-N-methylthionocarbamate,
(140) O-(4-trifluoromethylphenyl) N-(6-methoxy-2-pyridyl)-N-methylthionocarbamate,
(141) 1-(2-chlorobenzyl)-3-(a, a -dimethylbenzyl)urea,
(142) N-(3,5-dichlorophenyl)-1,2-dimethylcyclopropnae-1,2-dicarboximide,
(143) O-(2,6-dichloro-4-methoxyphenyl) O,O-dimethyl phosphorothioate,
(144) (E)-1-(2,4-dichlorophenyl)-4,4-dimethyl-2-(1H-1,2,4-triazol-1-yl)-1-penten-3-ol,
(145) isopropyl 3,4-diethoxyphenylcarbamate,
(146) N-[4-chloro-2-fluoro-5-(1-methyl-2-propynyloxy)-phenyl]-3,4,5,6-tetrahydrophthalimide,
(147) N-[4-chloro-2-fluoro-5-(pentyloxycarbonyl-methoxy) phenyl]-3,4,5,6-tetrahydrophthalimide,
(148) 7-fluoro-6-(3,4,5,6-tetrahydrophthalimide)-4-(2-propynyl)-1,4-benzoxazin-3(2H)-one,
(149) 2-[1-(ethoxyimino)ethyl]-3-hydroxy-5-[2-[4-(trifluoromethyl) phenylthio]ethyl]-2-cyclohexen-1-one,
(150) 1-(4-chlorophenyl)-3-(2,6-difluorobenzoyl)urea,
(151) isopropyl (2E,4E)-11-methoxy-3,7,11-trimethyl-2,4-dodecadienoate,
(152) 2-tert-butylimino-3-isopropyl-5-phenyl-3,4,5,6-tetrahydro-2H-1,3,5-triadiazin-4-one,
(153) 2-phenoxy-6-(neopentyloxymethyl)pyridine,
(154) 3-chloro-2-[7-fluoro-4-(2-propynyl)-3,4-dihydro-1,4-benzoxazin-3(2H)-on-6-yl]-4,5,6,7-tetrahydro-2H-indazole,
(155) 4'-chloro-2'-(α-hydroxybenzyl)isonicotinanilide,
(156) 6-(benzylamino)purine,
(157) 5-chloro-3-methyl-4-nitro-1H-pyrazole,
(158) 3-(4-chlorophenyl)-1,1-dimethylurea,
(159) 3-(3,4-dichlorophenyl)-1,1-dimethylurea,
(160) 2,-4-dinitro-6-sec-butylphenol,
(161) 2,4-dimethyl-5-(trifluoromethylsuofonylamino)-acetanilide,
(162) 6-(furfurylamino)purine,
(163) 1-phenyl-3-[4-(2-chloropyridyl)]urea,
(164) S,S-dimethyl 2-(difluoromethyl)-4-(2-methylpropyl)-6-(trifluoromethyl)pyridine-3,5-dicarbothioate,
(165) 3-(4,6-dimethoxy-1,3,5-triazin-2-yl)-1-[2-(2-methoxyethoxy) phenylsulfonyl]urea,
(166) exo-1-methyl-4-(1-methylethyl)-2-(2-methyl-phenylmethoxy)-7-oxabicyclo[2.2.1]heptane,
(167) 2',6'-diethyl-N-[(2-cis-butenoxy)methyl]-2-chloroacetanilide,
(168) 2,3-dihydro-3,3-dimethyl-5-benzofuranyl ethanesulfonate,
(169) 2',6'-dimethyl-N-(3-methoxy-2-thenyl)-2-chloroacetanilide,
(170) 1-(2-chloroimidazo[1,2-a]pyridin-3-ylsulfonyl)-3-(4,6-dimethoxy-2-pyrimidinyl)urea,
(171) 3-isopropyl-1H-2,1,3-benzothiadiazin-4(3H)-one-2,2-dioxide,
(172) 2-(1-ethoxyiminobutyl)-5-[2-(ethylthio)propyl]-3-hydroxycyclohex-2-en-1-one,
(173) 2',6'-diethyl-N-(2-propoxyethyl)-2-chloroacetanilide,
(174) S-(1-methyl-1-phenylethyl) piperidine-1-carbothioate,
(175) S-(2-methyl-1-piperidinecarbonylmethyl) O,O-dipropyl dithiophosphate.
(176) S-benzyl N-ethyl-N-(1,2-dimethylpropyl) thiolcarbamate,
(177) 2-chloro-4-ethylamino-6-isopropylamino-1,3,5-triazine,
(178) 2-methylthio-4,5-bis(ethylamino)-1,3,5-triazine,
(179) 2-chloro-4,6-bis(ethylamino)-1,3,5-triazine,
(180) 2-methylthio-4-ethylamino-6-(1,2-dimethylpropylamino)-1,3,5-triazine,
(181) 3-[2-(3,5-dimethyl-2-oxocyclohexyl)-2-hydroxy-methyl]glutarimide.
(182) 2-cyano-N-[1-(2,4-dichlorophenyl)-ethyl]-3,3-dimethyl-butanamide, and
(183) 5-amino-1-(2,6-dichloro-4-trifluoromethylphenyl)-3-cyano-4-trifluoromethansulfinylpyrazole.

The pesticidally active ingredient contained in the composition of the invention may be used alone or in admixture of two or more compounds according to the requirements. The content of the pesticidally active ingredient is generally 0.001 through 99% by weight: preferably 0.001 through 80% by weight, more preferably 0.01 through 50% by weight for the Composition A: preferably 0.01 through 80% by weight for the Composition B; and preferably 0.001 through 60% by weight for the Composition C.

Examples of the water-soluble alginate used in the invention are alkali metal salts of alginic acid such as sodium alginate and potassium alginate and ammonium salts of alginic acid. The alginic acid or water-soluble alginate may be used alone or in admixture of two or more of them.

Typical examples of the divalent or polyvalent cation which can convert an alginic acid or a water-soluble alginate into a water-insoluble alginate are calcium cation, magnesium cation, barium cation, zinc cation, nickel cation, copper cation, and lead cation. Examples of the aqueous solution containing the cation are that containing calcium salts such as aqueous solution of calcium chloride, calcium nitrate, calcium lactate, and calcium citrate, that containing magnesium salts such as aqueous solution of magnesium chloride, that containing barium salts such as aqueous solution of barium chloride, that containing zinc salts such as aqueous solution of zinc chloride, zinc nitrate, and zinc sulfate, that containing nickel salts such as aquous solution of nickel chloride, that containing copper salts such as aqueous solution of copper sulfate, and that containing lead salts such as aqueous solution of lead acetate. An aqueous solution of calcium chloride or calcium nitrate are preferable. The content of the cation salt is usually 1% by weight through saturated concentration , preferably 5% by weight through saturated concentration in aqueous solution. Although low-molecular through high-molecular weight water-soluble alginates and alginic acids can be used in the invention, the molecular weight of the alginic acid or water-soluble alginate is typically 500 through 8,000,000, preferably 3,000 through 2,000,000. The alginic acid or water-soluble alginate may be used in admixture of those having different molecular weights.

In case of coating the solid substance containing a pesticidally active ingredient directly with a water-insoluble alginate to yield the Composition B, calcium alginate, magnesium alginate, barium alginate, zinc alginate, nickel alginate, copper alginate, lead alginate, strontium alginate, cobalt alginate, or manganese alginate may be used as the water-insoluble alginate. Among them, calcium alginate is, however, most preferable for preparation of the Composition B. The water-insoluble alginate is used alone or in admixture of two or more of them.

The content of the alginic acid, water-soluble alginate, or water-insoluble alginate used for preparing the composition of the invention is generally 0.01 through 99.9% by weight based on the total weight of the composition of the invention: preferably 0.1 through 99.9% by weight, more preferably 5 through 70% by weight for the Composition A; preferably 0.01 through 50% by weight for the Composition B: and preferably 0.01 through 10% by weight, more preferably 0.05 through 5% by weight for the Composition C.

The composition of the invention may further contain a carrier, a surfactant, a solvent, a granulation improver, a binder, a stabilizer, a dye, a fragrance material, a synergist, a phytotoxicity reducer, and a lubricant according to the requirements.

Examples of the carrier which may be contained in the composition of the invention are: mineral carriers including kaolinite minerals such as kaolinite, dickite, nacrite, and haloysite, serpentines such as chrysotile, lizartite, antigorite, and amesite, smectites such as calcium montmorillonite, magnesium montmorillonite, saponite, hectorite, sauconite, and beidellite, magnesium silicates such as attapulgite and sepiolite, calcium carbonates such as dolomite: sulfate minerals such as gypsum and terra alba, mica clay minerals such as muscovite, phengite, sericite, and illite, silicas such as cristobalite and quartz, pyrophyllite, talc, pagodite, acid clay, activated clay, diatomaceous earth, pumice, silica sand, zeolite, vermiculite, ammonium sulfate, urea, ammonium chloride; synthetic inorganic carriers such as precipitated silicas, and calcined silicas: animal and vegetable carriers such as wheat flour, sucrose, dextrin, woodmeal, starch, rice bran, wheat bran, husks of grains, soybean meal, and carnauba wax; and waxes. Examples of waxes include: natural waxes such as candelilla wax, carnauba wax, rice wax, Japan wax, jojoba oil, beeswax, lanolin, spermaceti, beef tallow, ozokerite, and ceresin; petroleum waxes such as paraffin wax and microcrystalline wax: and synthetic waxes such as montan wax, polyethylene wax, fischer-tropsch wax, wax, hardened castor oil, 12-hydroxystearic acid, stearic acid, stearyl alcohol, lauron, stearone, isopropyl myristate, glycerol fatty acid esters, glycol fatty acid esters, and sorbitan fatty acid esters.

When the wax is used as a carrier, it may be heated to be melted in the process of mixing and/or granulation according to the requirements. After the composition is pre-granulated, melted wax may be added for final granulation.

The carrier may be used alone or in admixture of two or more of them. The content of the carrier is generally 0 through 99.9% by weight based on the total weight of the composition of the invention.

When the composition of the invention contains a liquid pesticidally active ingredient or additive in concentration of not less than 1% by weight based on the total weight of the composition, it is preferable to add white carbon to the composition. The preferable amount of white carbon is 40 through 100 parts by weight based on 100 parts by weight of the total liquid component. White carbon may also be added as a carrier even when the liquid component is less than 1% by weight.

The absorbent carrier used in preparation of the Composition C is a solid absorbent carrier having an oil absorption value (linseed oil absorption value in conformity with JIS K5101) of not less than 1 ml, preferably 5 through 60 ml based on 100 grams of the carrier. Examples of the absorbent carrier are: kaolinite minerals such as kaolinite, dickite, nacrite, and haloysite: serpentines such as chrysotile, lizartite, antigorite, and amesite; smectites such as calcium montmorillonite, magnesium montmorillonite, saponite, hectorite, sauconite, and beidellite: pyrophyllite; talc; pagodite: mica clay minerals such as muscovite, phengite, sericite, and illite; silicas such as cristobalite, quartz, silica sand, and silica balloon; magnesium silicates such as attapulgite and sepiolite; calcium carbonates such as dolomite, aragonite, and calcite: sulfate minerals such as gypsum, alum, and terra alba: zeolite; tuff; vermiculite: laponite: pumice: diatomaceous earth; cellulose; and husks of grains. Concrete examples are AGSORB LVM-NIS (attapulgite manufactured by OIL DRI Corp.), CELATOM (diatomaceous earth manufactured by EAGLE PICHER Corp.), ISHIKAWALITE (pumice manufactured by IshikawaLite Industries Co., Ltd.), BIODAC (cellulose complex manufactured by EDWARD LOWE INDUSTRIES Ltd.). Florex (attapulgite manufactured by Floridin Corp.). Celphere (cellulose manufactured by ASAHI CHEMICAL Co., Ltd.), Apls (diatomaceous earth manufactured by Isolite Insulating Products Co., Ltd.), and Isolite CG-1 (diatomaceous earth manufactured by Isolite Insulating Products Co., Ltd).

Preferable absorbent carriers are those non-disintegrable in water. The particle size is generally 0.2 through 30.0 mm, preferably 0.3 through 10 mm. The absorbent carrier may be used alone or in admixture of two or more of them. The content of the absorbent carrier is 30 through 99.8% by weight based on the total weight of the composition of the invention.

Examples of the surfactant used in the invention are: nonionic surfactants such as polyoxyethylene alkyl ethers, polyoxyethylene alkyl allyl ethers, polyoxyethylene lanolin alcohols, polyoxyethylene alkyl phenol formalin condensates, polyoxyethylene sorbitan fatty acid esters, polyoxyethylene glycerol mono-fatty acid esters, polyoxypropylene glycol mono-fatty acid esters, polyoxyethylene sorbitol fatty acid esters, polyoxyethylene-castor oil derivatives, polyoxyethylene fatty acid esters, fatty acid glycerol esters, sorbitan fatty acid esters, sucrose fatty acid esters, polyoxyethylene polyoxypropylene block polymers, polyoxyethylene fatty acid amides, alkylol amides, and polyoxyethylene alkyl amines; cationic surfactants such as alkylamine hydrochlorides such as dodecylamine hydrochloride, benzethonium chloride, alkyltrimethylammoniums such as dodecyltrimethylammonium, alkyldimethylbenzylammoniums, alkylpyridiniums, alkylisoquinoliniums, dialkylmorpholiniums, and polyalkylvinylpyridiniums: aninonic surfactants such as sodium salts of fatty acids such as sodium palmitate, ether sodium carboxylates such as polyoxyethylene lauryl ether sodium carboxylate, amino acid condensates of fatty acids such as lauroyl sodium sarcosine and N-lauroyl sodium glutamate, alkylarylsulfonates such as sodium dodecylbenzenesulfonate and diisopropylnaphthalenesulfonates, fatty acid ester sulfonates such as lauric acid ester sulfonates, dialkyl sulfosuccinates such as dioctyl sulfosuccinate, fatty acid amidosulfonates such as oleic acid amidosulfonate, formalin condensates of alkylarylsulfonates, alcohol sulfates such as pentadecane-2-sulfate, polyoxyethylene alkyl ether sulfates such as polyoxyethylene dodecyl ether sodium sulfate, polyoxyethylene alkyl phosphates such as dipolyoxyethylene dodecyl ether phosphates, styrene-maleic acid copolymers, and alkyl vinyl ether-maleic acid copolymers; and amphoteric surfactants such as N-laurylalanine, N,N,N-trimethylaminopropionic acid, N,N,N-trihydroxye thylaminopropionic acid, N-hexyl N,N-dimethylaminoacetic acid, 1-(2-carboxyethyl)-pyridiniumbetaine, and lecithin. The surfactant may be used alone or in admixture of two or more of them. The content of the surfactant is generally not more than 20% by weight, preferably 0.1 through 10% by weight, more preferably 0.1 through 5% by weight based on the total weight of the composition.

Examples of the solvent used in the invention are: saturated aliphatic hydrocarbons such as decane, tridecane, tetradecane, hexadecane, and octadecane: unsaturated aliphatic hydrocarbons such as 1-undecene and 1-henicosene: halogenated hydrocarbons such as Celeclor S45 (solvent manufactured by ICI Corp.), ketones such as acetone and methyl ethyl ketone: alcohols such as methanol, ethanol, butanol, and octanol: esters such as ethyl acetate, dimethyl phthalate, methyl laurate, ethyl palmitate, octyl acetate, dioctyl succinate, and didecyl adipate: aromatic hydrocarbons such as xylene, ethylbenzene, octadecylbenzene, dodecylnaphthalene, tr idecylnaphthalene, Hisol SAS-296 (solvent manufactured by Nippon Petrochemicals Co., Ltd.), Solvesso 100 (solvent manufactured by Exxon Chemical Corp.), and Solvesso 200 (solvent manufactured by Exxon Chemical Corp.); glycols, glycol esters, and glycol ethers such as ethylene glycol, diethylene glycol, propylene glycol monomethyl ether, and ethyl cellosolve; glycerol derivatives such as glycerol and glycerol fatty acid ester; fatty acids such as oleic acid, capric acid, and enanthic acid; polyglycols such as tetraethylene glycol, polyethylene glycol, and polypropylene glycol; amides such as N,N-dimethylformamide and diethylformamide: animal and vegetable oils such as olive oil, soybean oil, colza oil, castor oil, linseed oil, cottonseed oil, palm oil, avocado oil, and shark oil; and mineral oils such as machine oil. Among these solvents, those having solubility of not greater than 1% by weight in water at 20° C. are preferable.

The solvent may be used alone or in admixture of two or more of them. The content of the solvent is generally not greater than 50% by weight based on the total weight of the composition of the invention: preferably not greater than 30% by weight, more prefrably 0.1 through 20% by weight for the Composition A; preferably not greater than 30% by weight for the Composition B: and preferably not greater than 40% by weight, more preferably not greater than 10% by weight for the Composition C.

Examples of the granulation improver which may be used in the invention are: oils such as liquid paraffin, stearic acid, animal and vegetable oils, and mineral oils: surfactants such as alkyl benzenesulfonates, lignosulfonates, ethylenebisnaphthalene sulfonates, dialkylsulfosuccinates, and glycerol fatty acid esters; polyols and polymers thereof such as glycols, glycerol, and polyglycols; and water-soluble polymers such as polycarboxylic acids and polycarboxylates.

The granulation improver may be used alone or in admixture of two or more of them. The content of the granulation improver is generally not greater than 10% by weight, preferably not greater than 5% by weight based on the total weight of the composition of the invention.

Examples of the binder which may be used in the composition of the invention are: inorganic binders such as bentonite, montmorillonite, water-glass, and coloidal silica: natural organic binders such as starch, dextrin, casein, gelatin, hide glue, agar, gum arabic, corn starch, natural rubber, and pulp liquid; cellulose binders such as carboxymethylcellulose, sodium carbox ymethylcellulose, hydroxypropylmethylcellulose, methylcellulose, and ethylcellulose: synthetic resin binders such as polyvinyl alcohol, polyvinyl pyrrolidone, polyethylene glycol, vinyl acetate resin emulsions, vinyl chloride-vinyl acetate copolymer emulsions, acrylic resin emulsions, styrene-butadiene rubber emulsions, nitrile rubber emulsions, and polyvinyl chloride emulsions: and waxes including natural waxes, petroleum waxes, and synthetic waxes. It is preferable that wax used as a binder is previously heated to be melted or prepared to a wax-in-water emulsion.

The binder may be used alone or in admixture of two or more of them. The content of the binder is generally not greater than 50% by weight based on the total weight of the composition of the invention: preferably not greater than 40% by weight, more preferably 0.1 through 10% by weight for the Composition B; and not greater than 10% by weight for the Composition C.

When the Composition A is prepared according to the process of extrusion granulation, it is preferable to add bentonite to the Composition A for the effective granulation flow. The preferable bentonite used in the invention is sodium montmorillonite or sodium montmorillonite-containing bentonite. Concrete examples of the bentonite are Bentonite Fuji, Bentonite Hodaka, Bentonite Myogi, Bentonite Akagi, Bentonite Asama, BEN-GEL S, BEN-GEL HV (all manufactured by HOJUNYOKO Co., Ltd.), KUNIGEL V1 (manufactured by Kunimine Industries Co., Ltd.), and SK-ZERO-1 (manufactured by Nishige Kaihatsu). The content of the bentonite is determined according to the grade thereof and the type and the amount of the pesticidally active ingredient, but generally 1 through 50% by weight, preferably 5 through 30% by weight based on the total weight of the Composition A.

Typical examples of the stabilizer which may be used in the invention are antioxidants, light stabilizers, ultraviolet stabilizers, radical scabengers, and peroxide decomposers. Examples of the antioxidant are antioxidants of phenol type, amine type, phosphorus type, and sulfur type antioxidants. Examples of the ultraviolet stabilizer are that of benzotriazole type, cyanoacrylate type, salicylic acid type, and hindered amine type. Isopropyl acid phosphate, liquid paraffin, and epoxidized vegetable oils like epoxidized soybean oil, linseed oil, and colza oil may also be used as the stabilizer. The stabilizer may be used alone or in admixture of two or more of them. The content of the stabilizer is generally not greater than 10% by weight based on the total weight of the composition of the invention: preferably not greater than 5% by weight for the Composition C.

Examples of the dye which may be used in the composition are a rhodamine like rhodamine B or solar rhodamine or a synthetic organic food additive like Yellow No. 4, Blue No. 1, or Red No. 2. Examples of the fragrance material are: esters such as ethyl acetoacetate, methyl anthranilate, isoamyl isovalerate, ethyl enanthate, ethyl cinnamate, and isoamyl butyrate; organic acids such as caproic acid, and cinnamic acid; alcohols such as cinnamalcohol, geraniol, citral, decyl alcohol, and menthol: aldehydes such as vanillin, piperonal, peryl aldehyde; and ketones such as maltol and methyl 8-naphthyl ketone. The contents of the dye and the fragrance material are respectively not greater than 5% by weight based on the total weight of the composition of the invention.

The Composition A is prepared in the following manner. A pesticidally active ingredient is mixed first with an alginic acid or a water-soluble alginate and further with a synergist, a phytotoxicity reducer, a carrier, a surfactant, a solvent, a granulation improver, a binder, a stabilizer, a dye, a fragrance material, a lubricant, and a bentonite according to the requirements. The mixture is granulated by the process of extrusion granulation, pan granulation, compaction granulation, mixing granulation, or fluidized bed granulation. The granules are further disintegrated, sieved, or processed to desirable shapes and size according to the requirements. The solid composition thus obtained is treated with an aqueous solution containing a divalent or polyvalent cation, so that the alginic acid or water-soluble alginate contained in the solid composition is converted to the water-insoluble alginate. After the treatment, the composition is dried, sieved, and processed to desirable shapes and size according to the requirements.

Processes applicable to manufacture the composition of the invention are extrusion granulation, pan granulation, compaction granulation, mixing granulation, spray-drying granulation, fluidized bed granulation, and vacuum freeze-drying granulation.

A typical process of extrusion granulation is given below.

Components of the composition are mixed well with an appropriate blender, for example, a ribbon blender, a Henschel mixer, a pan mixer, a paddle mixer, a screw mixer, a Horberg mixer, a spiral mixer, or a V-type blender. The mixture obtained is sufficiently kneaded with a ribbon blender or a kneader after water, a binder, an aqueous solution of binder, or an organic solvent solution of a binder is added to the mixture according to the requirements. The kneaded mixture is then granulated with an appropriate extrusion granulator, for example, a screw-type extrusion granulator, a roll-type extrusion granulator, a disc pelletizer, a pellet mill, a basket-type extrusion granulator, a blade-type extrusion granulator, an oscillating extrusion granulator, a gear-type extrusion granulator, or a ring die-type extrusion granulator. The granules thus obtained are processed to desirable size and shapes with a shape control machine, a disintegrating machine, or a sieve.

A typical process of pan granulation is given below.

Components of the composition are mixed well with an appropriate blender like the extrusion granulation process. The mixture is granulated with an appropriate pan granulator, for example, an inclined disc-type pan granulator or a drum-type pan granulator, while water, a binder, an aqueous solution of binder, or an organic solvent solution of a binder is added to the mixture according to the requirements. The granules thus obtained are processed to desirable size and shapes with a disintegrating machine or a sieve according to the requirements.

A typical process of compaction granulation is given below.

Components of the composition are mixed well with an appropriate blender like the extrusion granulation process. The mixture is directly granulated with an appropriate compaction granulator (dry granulation). Alternatively, the mixture is granulated with an appropriate compaction granulator after water, a binder, an aqueous solution of binder, or an organic solvent solution of a binder is added to the mixture and kneaded sufficiently (wet granulation). Wet compaction granulation is preferable in general. The compaction granulator used here may be a roller compactor, a rotary pelletizer, a bricketing machine, or a compacting machine. The granules thus obtained are processed to desirable size and shapes with a shape control machine, a disintegrating machine, or a sieve according to the requirements.

A typical process of mixing granulation is given below.

Components of the composition are mixed well with an appropriate blender like the extrusion granulation process. The mixture is granulated with an appropriate blending granulator while water, a binder, an aqueous solution of binder, or an organic solvent solution of a binder is added to the mixture according to the requirements. Examples of the blending granulator used herein are a blender with granulation blades, a blender granulator, a pin granulator, a blending granulator with high-speed blending blades, or a flexomixer. The granules thus obtained are processed to desirable size and shapes with a disintegrating machine or a sieve according to the requirements.

A typical process of spray-drying granulation is given below.

Components of the composition are mixed well with an appropriate blender for example, a paddle mixer, a screw-mixer, or V-type blender. The aqueous solution, oil-in-water emulsion, or aqueous suspension thus obtained is sprayed and dried to granules with an appropriate spray-drying granulator like a spray dryer. The granules thus obtained are processed to desirable size and shapes with a disintegrating machine or a sieve according to the requirements.

A typical process of fluidized bed granulation is given below.

Components of the composition are mixed well with an appropriate blender like the extrusion granulation process. The mixture is granulated with an appropriate fluidized bed granulator after water, a binder, an aqueous solution of a binder, or an organic solvent solution of a binder is added to the mixture according to the requirements. The granules thus obtained are processed to desirable size and shapes with a disintegrating machine or a sieve according to the requirements.

A typical process of freeze-drying granulation is given below.

Components of the composition are mixed well with an appropriate blender such as a paddle mixer, a screw mixer, and a V-type blender. The aqueous solution, oil-in-water emulsion, or aqueous suspension thus obtained is dried to granules with an appropriate freeze-drying granulator like rotor freezer or a belt freezer. The granules thus obtained are processed to desirable size and shapes with a disintegrating machine or a sieve.

The solid composition thus obtained is treated with a cation solution for conversion of an alginic acid or water-soluble alginate contained in the solid composition into a water-insoluble alginate. According to the method, the solid composition is immersed and left in an aqueous solution containing a divalent or polyvalent cation which can convert alginic acid or a water-soluble alginate into a water-insoluble alginate (hereinafter referred to as conversion solution), for example, for one minute to five hours. Other possible methods of the conversion include: impregnating the solid composition with the conversion solution with stirring: and spraying or dropping the conversion solution onto the solid composition for treating the solid composition with the conversion solution. The method of immersing the solid composition in the conversion solution is preferable. The amount of the conversion solution used herein is varied depending upon the conversion method applied, the recipe of the solid composition, and the concentration of the cation in the conversion solution, but generally 0.001 through 10 parts by weight (as the weight of the cation salt) based on 1 part by weight of the solid composition.

The treated solid composition is then dried and processed to the Composition A of desirable shapes and size according to the requirements.

The Composition B is prepared in the following manner. A pesticidally active ingredient is mixed with a carrier, a synergist, a phytotoxicity reducer, a stabilizer, a dye, a fragrance material, a binder, a surfactant, a solvent, and a lubricant according to the requirements. The mixture is then granulated by the process of extrusion granulation, pan granulation, compaction granulation, mixing granulation, coating granulation, spray-drying granulation, fluidized bed granulation, or freeze-drying granulation. The granules are further disintegrated, sieved, or processed to desirable shapes and size according to the requirements. The solid substance thus obtained is coated with a water-insoluble alginate. Alternatively, the solid substance is first coated with an alginic acid or a water-soluble alginate and then the solid composition is treated with the conversion solution, so that the alginic acid or water-soluble alginate coating the solid composition is converted into the water-insoluble alginate. The latter method is preferable in general. It is preferable that a binder is used with a water-insoluble alginate, powder of alginic acid, or powder of water-soluble alginate when the solid substance is coated with the water-insoluble alginate, alginic acid, or water-soluble alginate.

The pesticidally active ingredient-containing solid substance is coated with a water-insoluble alginate, for example, according to the following method. A water-insoluble alginate and a binder is added to the solid substance and mixed sufficiently, so that the solid substance is coated with the water-insoluble alginate. Although the water-insoluble alginate may be any of calcium, magnesium, barium, zinc, nickel, copper, lead, strontium, cobalt, and manganese alginates, calcium alginate is preferable. The binder used herein may be selected out of those listed above and carboxymethylcellulose, ethylcellulose, synthetic resin binders such as vinyl acetate resin emulsions are preferable. The binders may be used to be dissolved in water or an appropriate solvent.

The pesticidally active ingredient-containing solid substance is coated with an alginic acid or water-soluble alginate and then treated with an aqueous solution containing a divalent or polyvalent cation which can convert the alginic acid or water-soluble alginate into a water-insoluble alginate, for example, according to the following method.

The solid substance is coated with an alginic acid or water-soluble alginate by immersing the solid substance in an aqueous solution of the alginic acid or water-soluble alginate, spraying the aqueous solution onto the solid substance, or adding a mixture of the alginic acid or water-soluble alginate and a binder to the solid substance. The solid composition thus obtained is then treated with the conversion solution in the same manner as the process of manufacturing the Composition A, so that the alginic acid or water-soluble alginate is converted into a water-insoluble alginate. The solid composition thus treated is then dried and processed to the Composition B of desirable shapes and size according to the requirements.

The Composition C is manufactured in the following manner. A solid substance containing a pesticidally active ingredient is prepared by mixing the pesticidally active ingredient with an absorbent carrier and further with a solvent, a surfactant, a binder, a stabilizer, a phytotoxicity reducer, and a synergist according to the requirements. For example, while the absorbent carrier was blended with a blender used in the extrusition granulation process, liquid pesticidally active ingredient or a solution of the pesticidally active ingredient is dropped or sprayed onto the absorbent carrier to obtain the solid substance, and then the solid substance is dried according to the requirements. The solid substance thus obtained is impregnated with an alginic acid or water-soluble alginate to obtain a solid composition. The solid composition may be obtained by mixing a pesticidally active ingredient, an absorbent carrier and an alginic acid or a water-soluble alginate and further necessary component at the same time. The former method for preparing the solid composition is preferable. Examples of the method of impregnating are dropping or spraying an aqueous solution of an alginic acid or a water-soluble alginate onto the solid substance while the solid substance is blended, and immersing the solid substance in an aqueous solution of an alginic acid or water-soluble alginate. The concentration of the alginic acid or water-soluble alginate in an aqueous solution is usually 0.01 through 20% by weight, preferably 0.1 through 10% by weight. The aqueous solution of the alginic acid or the water-soluble alginate may be heated. The solid composition is then treated with the conversion solution in the same manner as the process of manufacturing the Composition A, so that the alginic acid or water-soluble alginate is converted into a water-insoluble alginate. The solid composition thus treated is dried and processed to the Composition C of desirable shapes and size according to the requirements.

The composition of the invention is a solid, for example, microgranules, particles, granules, tablets, pellets, or blocks, and generally has the particle diameter of 0.05 through 500 mm, preferably 0.2 through 500 mm and, in water stream, more preferably 2 through 500 mm. The composition is processed to have any desirable shape such as sphere, ellipsoid, disc, bar, dumbbell, cylinder, polygonal prism, cone, multilateral pyramid, cube, quadratic prism, capsule, finger, almond, lens, square-cornered disc, round-cornered disc, and amorphism.

The composition of the invention is applied to the agricultural or horticultural field such as flowerpots, nurseries, rice paddies, fields, grass, orchards, woods and forests, or the aqueous environments or the water stream such as rivers, ponds, lakes, swamps, canals, reservoirs, waterworks, sewers, ditches, water channels, underground waterways, another several aquous environments and surroundings thereof in conformity with conventional application of pesticides.

When the composition of the invention is applied to the water streams such as rivers, waterworks, sewers, canals, ditches, water channels, underground waterways, and inlets into rice paddies, it is preferable that the particle diameter of the composition is relatively large, for example 0.2 through 500 mm, and the composition is applied directly or put in mesh-bags.

The amount of the composition of the invention may, vary depending upon the kind of the active ingredient, the weather condition, the timing of applying, the method of applying, the place of applying, the target for controlling or regulating and the like. Generally, the amount of the active ingredient is 0.01 through 1000 g, preferably, 0.01 through 100 g per 1 $m^2$ in case of insecticide, acaricide or nematocide; 0.001 through 1 g per 1 $m^2$ in case of insect growth regulator; 1 g through 10 Kg per 1 ha in case of fungicide or herbicide; and 0.001 g through 10 g per 1 ha in case of plant growth regulator.

The invention is described more in detail with Preparation Examples, Reference Examples and Test Examples below, though the invention is not limited to the Examples in any sense. In the description of the Examples, parts and % respectively denote parts by weight and % by weight, and each pesticidally active ingredient is shown by the reference number of the compound.

PREPARATION EXAMPLE 1

Three parts of a pesticidally active ingredient (90) were mixed with 0.6 parts of white carbon and ground by a centrifugal grinder (Model ZM-1: manufactured by Nihon Seiki Manufacturing Ltd). Five parts of sodium alginate and clay were added successively to the ground mixture to the total amount of 100 parts and mixed well with a blender. The mixture was kneaded with 20 parts of water by a chemical mixer (Model H-85: manufactured by Kokusan Enshinki Co., Ltd.) and granulated to granules having the average diameter of 1.5 mm with an extrusion granulator. After the granules were dried at 50° C. for 1 hour, those of 1.2 through 1.8 mm in diameter were separated with a sieve. The sieved granules were immersed in a 20% aqueous solution of calcium chloride for 60 minutes and subsequently dried to yield the Composition (1) of the invention.

PREPARATION EXAMPLE 2

The Composition (2) of the invention was prepared in the same manner as Preparation Example 1 except that 10 parts of sodium alginate were used instead of 5 parts of the same.

PREPARATION EXAMPLE 3

The Composition (3) of the invention was prepared in the same manner as Preparation Example 1 except that 20 parts of sodium alginate were used instead of 5 parts of the same.

PREPARATION EXAMPLE 4

The Composition (4) of the invention was prepared in the same manner as Preparation Example 1 except that 40 parts of sodium alginate were used instead of 5 parts of the same.

PREPARATION EXAMPLE 5

The Composition (5) of the invention was prepared in the same manner as Preparation Example 1 except that 60 parts of sodium alginate were used instead of 5 parts of the same.

PREPARATION EXAMPLE 6

Ten parts of a pesticidally active ingredient (90) were mixed with 2 parts of white carbon and ground by a centrifugal grinder (Model ZM-1: manufactured by Nihon Seiki Manufacturing Ltd). Seventy parts of sodium alginate and clay were added successively to the ground mixture to the total amount of 100 parts and mixed well with a blender. The mixture was kneaded with 35 parts of water by a chemical mixer (Model H-85: manufactured by Kokusan Enshinki Co., Ltd.) and granulated to granules having the average diameter of 1.5 mm with an extrusion granulator. After the granules were dried at 50° C. for 1 hour, those of 1.2 through 1.8 mm in diameter were separated with a sieve. The sieved granules were immersed in a 20% aqueous solution of calcium chloride for 1 hour and subsequently dried to yield the Composition (6) of the invention.

PREPARATION EXAMPLE 7

Ten parts of a pesticidally active ingredient (117) were mixed with 2 parts of white carbon and ground by a centrifugal grinder (Model ZM-1: manufactured by Nihon Seiki Manufacturing Ltd). Twenty five parts of sodium alginate and clay were added successively to the ground mixture to the total amount of 100 parts and mixed well with a blender. The mixture was kneaded with 20 parts of water by a chemical mixer (Model H-85: manufactured by Kokusan Enshinki Co., Ltd.) and granulated to granules having the average diameter of 0.7 mm with an extrusion granulator. After the granules thus obtained were dried at 50° C. for 1 hour, immersed in a 20% aqueous solution of calcium nitrate for 10 minutes, and dried again to yield the Composition (7) of the invention.

PREPARATION EXAMPLE 8

The Composition (8) of the invention was prepared in the same manner as Preparation Example 7 except that 50 parts of sodium alginate were used instead of 25 parts of the same.

PREPARATION EXAMPLE 9

The Composition (9) of the invention was prepared in the same manner as Preparation Example 7 except that 4 parts of the pesticidally active ingredient (117), 0.8 parts of white carbon, and 5 parts of sodium alginate were used respectively in place of 10 parts, 2 parts, and 25 parts of the same and that the average particle diameter was not 0.7 mm but 0.9 mm.

PREPARATION EXAMPLE 10

The Composition (10) of the invention was prepared in the same manner as Preparation Example 7 except that 4 parts of the pesticidally active ingredient (117), 0.8 parts of white carbon, and 10 parts of sodium alginate were used respectively in place of 10 parts, 2 parts, and 25 parts of the same and that the average particle diameter was not 0.7 mm but 0.9 mm.

PREPARATION EXAMPLE 11

The Composition (11) of the invention was prepared in the same manner as Preparation Example 7 except that 4 parts of the pesticidally active ingredient (117), 0.8 parts of white carbon, and 20 parts of sodium alginate were used respectively in place of 10 parts, 2 parts, and 25 parts of the same and that the average particle diameter was not 0.7 mm but 0.9 mm.

PREPARATION EXAMPLE 12

Four parts of a pesticidally active ingredient (117) were mixed with 0.8 part of white carbon and ground by a centrifugal grinder (Model ZM-1: manufactured by Nihon Seiki Manufacturing Ltd). Twenty parts of sodium alginate and clay were added successively to the ground mixture to the total amount of 100 parts and mixed well with a blender. The mixture was kneaded with 20 parts of water by a chemical mixer (Model H-85: manufactured by Kokusan Enshinki Co., Ltd.) and granulated to granules having the average diameter of 1.2 mm with an extrusion granulator. After the granules thus obtained were dried at 50° C. for 1 hour, immersed in a 20% aqueous solution of calcium nitrate for 10 minutes, and dried again to yield the Composition (12) of the invention.

PREPARATION EXAMPLE 13

Clay was added to a mixture consisting of 5 parts of a pesticidally active ingredient (43), 5 parts of white carbon, and 7.5 parts of sodium alginate to the total amount of 100 parts and mixed well with a blender. The mixture was kneaded with 20 parts of water by a chemical mixer (Model H-85: manufactured by Kokusan Enshinki Co., Ltd.) and granulated to granules having the average diameter of 0.9 mm with an extrusion granulator. The granules were dried at 50° C. for 1 hour, immersed in a 10% aqueous solution of calcium nitrate for 10 minutes, and dried again to yield the Composition (13) of the invention.

PREPARATION EXAMPLE 14

The Composition (14) of the invention was prepared in the same manner as Preparation Example 13 except that 20 parts of sodium alginate were used instead of 7.5 parts of the same.

PREPARATION EXAMPLE 15

Clay was added to a mixture consisting of 3 parts of a pesticidally active ingredient (114), 10 parts of phenylxylylethane, 10 parts of white carbon, and 3 parts of sodium alginate to the total amount of 100 parts and mixed well with a blender. The mixture was kneaded with 20 parts of water by a chemical mixer (Model H-85: manufactured by Kokusan Enshinki Co., Ltd.) and granulated to granules having the average diameter of 1.2 mm with an extrusion granulator. The granules thus obtained were dried at 50° C. for 1 hour, immersed in a 20% aqueous solution of calcium chloride for 20 minutes, and dried again to yield the Composition (15) of the invention.

PREPARATION EXAMPLE 16

The Composition (16) of the invention was prepared in the same manner as Preparation Example 15 except that 30 parts of sodium alginate were used instead of 5 parts of the same.

PREPARATION EXAMPLE 17

Five parts of a pesticidally active ingredient (90) were mixed with 1 part of white carbon and ground by a centrifugal grinder (Model ZM-1: manufactured by Nihon Seiki Manufacturing Ltd). Ten parts of sodium alginate and clay were added successively to the ground mixture to the total amount of 100 parts and mixed well with a blender. The mixture was kneaded with 10 parts of water by a chemical mixer (Model H-85: manufactured by Kokusan Enshinki Co., Ltd.) and granulated to 1-gram cylindrical tablets with a compaction granulator.

The tablets thus obtained were immersed in a 10% aqueous solution of calcium chloride for 5 minutes and dried to yield the Composition (17) of the invention.

PREPARATION EXAMPLE 18

Five parts of a pesticidally active ingredient (90) were mixed with 1 part of white carbon and ground by a centrifugal grinder (Model ZM-1: manufactured by Nihon Seiki Manufacturing Ltd). Twenty parts of sodium alginate and clay were added successively to the ground mixture to the total amount of 100 parts and mixed well with a blender. The mixture was kneaded with 15 parts of water by a chemical mixer (Model H-85: manufactured by Kokusan Enshinki Co., Ltd.) and granulated to 2-gram cylindrical tablets with a rotary tabletizer. The tablets thus obtained were immersed in a 10% aqueous solution of calcium chloride for 5 minutes and dried to yield the Composition (18) of the invention.

PREPARATION EXAMPLE 19

Five parts of a pesticidally active ingredient (90) were mixed with 1 part of white carbon and ground by a centrifugal grinder (Model ZM-1: manufactured by Nihon Seiki Manufacturing Ltd). Twenty parts of sodium alginate and clay were added successively to the ground mixture to the total amount of 100 parts. While 5 parts of ethylene-vinyl acetate emulsion were added, the mixture was granulated under blending in a mixing granulator. Resultant granules of 0.5 through 1.0 mm in diameter were separated with a sieve, immersed in a 10% aqueous solution of calcium chloride for 5 minutes, and dried to yield the Composition (19) of the invention.

PREPARATION EXAMPLE 20

The Composition (20) of the invention was prepared in the same manner as Preparation Example 19 except that 5 parts of 1% aqueous polyvinyl alcohol with saponification value of 75% were used instead of 5 parts of ethylene-acetate vinyl emulsion.

PREPARATION EXAMPLE 21

1.5 parts of a pesticidally active ingredient (90) were mixed with 0.3 part of white carbon and ground by a centrifugal grinder (Model ZM-1: manufactured by Nihon Seiki Manufacturing Ltd). Ten parts of sodium alginate and clay were added successively to the ground mixture to the total amount of 100 parts and mixed well with a blender. The mixture was kneaded with 20 parts of water by a chemical mixer (Model H-85: manufactured by Kokusan Enshinki Co., Ltd.) and granulated to granules having the average diameter of 0.9 mm with an extrusion granulator. The granules were immersed in a 20% aqueous solution of calcium chloride for 30 minutes and subsequently dried to yield the Composition (21) of the invention.

PREPARATION EXAMPLE 22

The Composition (22) of the invention was prepared in the same manner as Preparation Example 21 except that 20 parts of sodium alginate were used instead of 10 parts of the same.

PREPARATION EXAMPLE 23

Clay was added to a mixture consisting of 10.5 parts of a pesticidally active ingredient (112), 8 parts of white carbon, and 5 parts of sodium alginate to the total amount of 100 parts and mixed well with a blender. The mixture was kneaded with 20 parts of water by a chemical mixer (Model H-85: manufactured by Kokusan Enshinki Co., Ltd.) and granulated to granules having the average diameter of 0.5 mm with an extrusion granulator. The granules thus obtained were immersed in a 20% aqueous solution of calcium chloride for 10 minutes and dried to yield the Composition (23) of the invention.

PREPARATION EXAMPLE 24

The Composition (24) of the invention was prepared in the same manner as Preparation Example 23 except that 20 parts of sodium alginate were used instead of 5 parts of the same.

PREPARATION EXAMPLE 25

Clay was added to a mixture consisting of 3.5 parts of a pesticidally active ingredient (112), 3 parts of white carbon, and 5 parts of sodium alginate to the total amount of 100 parts and mixed well with a chemical mixer (Model H-85: manufactured by Kokusan Enshinki Co., Ltd). The mixture was kneaded with 15 parts of water and granulated to granules having the average diameter of 10 mm with an extrusion granulator. The granules thus obtained were dried with a fluidized bed drier at 50° C. for 30 minutes, immersed in a-10% aqueous solution of calcium chloride for 20 minutes, and dried again at 50° C. for 30 minutes to yield the Composition (25) of the invention.

PREPARATION EXAMPLE 26

The Composition (26) of the invention was prepared in the same manner as Preparation Example 25 except that 20 parts of sodium alginate were used instead of 5 parts of the same.

PREPARATION EXAMPLE 27

Clay was added to a mixture consisting of 3.5 parts of a pesticidally active ingredient (112), 3 parts of white carbon, and 40 parts of sodium alginate to the total amount of 100 parts and mixed well with a chemical mixer (Model H-85: manufactured by Kokusan Enshinki Co., Ltd). The mixture was kneaded with 25 parts of water and granulated to granules having the average diameter of 20 mm with an extrusion granulator. The granules thus obtained were dried with a fluidized bed drier at 50° C. for 30 minutes, immersed in a 10% aqueous solution of calcium chloride for 30 minutes, and dried again at 50° C. for 30 minutes to yield the Composition (27) of the invention.

PREPARATION EXAMPLE 28

The Composition (28) of the invention was prepared in the same manner as Preparation Example 27 except that 80 parts of sodium alginate were used instead of 40 parts of the same.

PREPARATION EXAMPLE 29

Fine powder of calcium carbonate was added to a mixture of 2 parts of a pesticidally active ingredient (117) and 10 parts of sodium alginate to the total amount of 100 parts and mixed well with a chemical mixer (Model H-85: manufactured by Kokusan Enshinki Co., Ltd). The mixture was kneaded with 15 parts of water and granulated to granules having the average diameter of 10 mm with an extrusion granulator. The granules thus obtained were immersed in a 20% aqueous solution of calcium nitrate for 5 minutes and dried at 50° C. for 30 minutes in a fluidized bed dryer to yield the Composition (29) of the invention.

PREPARATION EXAMPLE 30

Clay was added to a mixture consisting of 2 parts of a pesticidally active ingredient (117), 30 parts of sodium alginate, and 2 parts of sodium dodecylbenzenesulfonate to the total amount of 100 parts and mixed well with a chemical mixer (Model H-85: manufactured by Kokusan Enshinki Co., Ltd). The mixture was kneaded with 15 parts of water and granulated to granules having the average diameter of 40 mm with an extrusion granulator. The granules thus obtained were immersed in a 20% aqueous solution of calcium nitrate for 5 minutes and dried at 50° C. for 30 minutes in a fluidized bed dryer to yield the Composition (30) of the invention.

PREPARATION EXAMPLE 31

Fine powder of calcium carbonate was added to a mixture consisting of 2 parts of a pesticidally active ingredient (117), 40 parts of sodium alginate, and 1 part of polyoxyethylenestyryl phenyl ether (9 moles by polyoxyethylene) to the total amount of 100 parts and mixed well with a chemical mixer (Model H-85: manufactured by Kokusan Enshinki Co., Ltd). The mixture was kneaded with 25 parts of water and granulated to granules having the average diameter of 50 mm with an extrusion granulator. The granules thus obtained were immersed in a 20% aqueous solution of calcium nitrate for 10 minutes and dried at 50° C. for 30 minutes in a fluidized bed dryer to yield the Composition (31) of the invention.

PREPARATION EXAMPLE 32

Six parts of a pesticidally active ingredient (117) were mixed with 1.2 part of white carbon and ground by a centrifugal grinder (Model ZM-1: manufactured by Nihon Seiki Manufacturing Ltd). Twenty parts of sodium alginate, 2 parts of Gohsenol NL-05 (polyvinyl alcohol manufactured by The Nippon Synthetic Chemical Industry Co., Ltd), and clay were added successively to the ground mixture to the total amount of 100 parts and mixed well with a chemical mixer (Model H-85: manufactured by Kokusan Enshinki Co., Ltd). The mixture was kneaded with 25 parts of water, and 20 grams of the kneaded mixture were molded to a product having a diameter of 50 mm in a cylindrical mold of 50 mm in diameter. The product thus obtained was immersed in a 20% aqueous solution of calcium nitrate for 10 minutes and dried at 50° C. for 30 minutes in a fluidized bed dryer to yield the Composition (32) of the invention.

PREPARATION EXAMPLE 33

Fine powder of calcium carbonate was added to a mixture consisting of 10.5 parts of a pesticidally active ingredient (112), 6 parts of another pesticidally active ingredient (117), 10 parts of white carbon, 10 parts of sodium alginate, I part of sodium dodecylbenzenesulfonate, and 2 parts of stearic acid to the total amount of 100 parts and mixed well with a chemical mixer (Model H-85: manufactured by Kokusan Enshinki Co., Ltd). The mixture was kneaded with 30 parts of water, and 30 grams of the kneaded mixture were molded to a product having a diameter of 60 mm in a cylindrical mold of 60 mm in diameter. After 20 parts of a 10% aqueous solution of calcium chloride were sprayed onto the product obtained, the sprayed product was dried at 50° C. for 30 minutes in a fluidized bed dryer to yield the Composition (33) of the invention.

PREPARATION EXAMPLE 34

Clay was added to a mixture consisting of 10.5 parts of a pesticidally active ingredient (112), 6 parts of another pesticidally active ingredient (117), 10 parts of white carbon, and 40 parts of sodium alginate to the total amount of 100 parts and mixed well with a chemical mixer (Model H-85: manufactured by Kokusan Enshinki Co., Ltd). The mixture was kneaded with 30 parts of water, and 45 grams of the kneaded mixture were tableted to a tablet having a diameter of 30 mm in a mold of 30 mm in diameter. The tablet thus obtained was immersed in a 20% aqueous solution of calcium nitrate for 30 minutes and dried at 50° C. for 30 minutes in a fluidized bed dryer to yield the Composition (34) of the invention.

PREPARATION EXAMPLE 35

Fine powder of calcium carbonate was added to a mixture consisting of 10.5 parts of a pesticidally active ingredient (112), 6 parts of another pesticidally active ingredient (117), 10 parts of white carbon, 20 parts of sodium alginate, 1 part of sodium dodecylbenzenesulfonate, and 1 parts of stearic acid to the total amount of 100 parts and mixed well with a chemical mixer (Model H-85: manufactured by Kokusan Enshinki Co., Ltd). The mixture was kneaded with 25 parts of water, and 400 grams of the kneaded mixture were molded to a product having a diameter of 100 mm in a cylindrical mold of 100 mm in diameter. After 20 parts of a 10% aqueous solution of calcium chloride were sprayed onto the product obtained, the sprayed product was dried at 50° C. for 30 minutes in a fluidized bed dryer to yield the Composition (35) of the invention.

PREPARATION EXAMPLE 36

Clay was added to a mixture of 0.01 part of a pesticidally active ingredient (114) and 5 parts of sodium alginate to the total amount of 100 parts and mixed well with a chemical mixer (Model H-85: manufactured by Kokusan Enshinki Co., Ltd). While 10 parts of water were added, the mixture was granulated to granules having the average diameter of 20 mm with mixing granulator. The granules thus obtained were dried at 50° C. for 30 minutes in a fluidized bed dryer. The granules were then treated with 30 parts of a 20% aqueous solution of calcium nitrate by sprayng, and dried at 50° C. for 30 minutes in the fluidized bed dryer to yield the Composition (36) of the invention.

PREPARATION EXAMPLE 37

Clay was added to a mixture consisting of 0.1 part of a pesticidally active ingredient (114), 0.5 part of phenylxylylethane, 1 part of white carbon, and 10 parts of sodium alginate to the total amount of 100 parts and mixed well with a chemical mixer (Model H-85: manufactured by Kokusan Enshinki Co., Ltd). The mixture was kneaded with 20 parts of water, and 1,500 grams of the kneaded mixture were molded to a product having a diameter of 200 mm in a cylindrical mold of 200 mm in diameter. The product was then treated with 30 parts of a 20% aqueous solution of calcium nitrate by spraying, and dried at 50° C. for 30 minutes in a fluidized bed dryer to yield the Composition (37) of the invention.

PREPARATION EXAMPLE 38

Clay was added to a mixture of 0.01 part of a pesticidally active ingredient (115) and 1 part of sodium alginate to the total amount of 100 parts and mixed well with a chemical mixer (Aodel H-85: manufactured by Kokusan Enshinki Co., Ltd). The mixture was kneaded with 15 parts of water and granulated to granules having the average diameter of 10 mm with an extrusion granulator. The granules thus obtained were then treated with 30 parts of a 20% aqueous solution of calcium nitrate by spraying, and dried at 50° C. for 30 minutes in a fluidized bed dryer to yield the Composition (38) of the invention.

PREPARATION EXAMPLE 39

Fine powder of calcium carbonate was added to a mixture of 0.01 part of a pesticidally active ingredient (115) and 50 parts of sodium alginate to the total amount of 100 parts and mixed well with a chemical mixer (Model H-85: manufactured by Kokusan Enshinki Co., Ltd) While 30 parts of water were added, the mixture was granulated to granules having the average diameter of 30 mm under blending in an blending granulator. The granules thus obtained were immersed in a 20% aqueous solution of calcium nitrate for 2 hours and dried at 50° C. for 30 minutes in a fluidized bed dryer to yield the Composition (39) of the invention.

PREPARATION EXAMPLE 40

Clay was added to a mixture of 0.01 part of a pesticidally active ingredient (115) and 99 parts of sodium alginate to the total amount of 100 parts and mixed well with a chemical mixer (Model H-85: manufactured by Kokusan Enshinki Co., Ltd). The mixture was kneaded with 50 parts of water and granulated to granules having the average diameter of 10 mm with an extrusion granulator. The granules thus obtained were immersed in a 20% aqueous solution of calcium nitrate for 30 minutes and dried at 50° C. for 30 minutes in a fluidized bed dryer to yield the Composition (40) of the invention.

PREPARATION EXAMPLE 41

Sodium alginate was added to 60 parts of a pesticidally active ingredient (115) to the total amount of 100 parts and mixed well with a chemical mixer (Model H-85: manufactured by Kokusan Enshinki Co., Ltd). The mixture was kneaded with 30 parts of water and granulated to granules having the average diameter of 25 mm with an extrusion granulator. The granules thus obtained were dried at 50° C. for 30 minutes in a fluidized bed dryer. The granules were then treated with 20 parts of a 10% aqueous solution of calcium chloride by spraying, and dried again at 50° C. for 30 minutes in the fluidized bed dryer to yield the Composition (41) of the invention.

PREPARATION EXAMPLE 42

Clay was added to a mixture consisting of 5 parts of a pesticidally active ingredient (43), 5 parts of white carbon, and 20 parts of sodium alginate to the total amount of 100 parts and mixed well with a chemical mixer (Model H-85: manufactured by Kokusan Enshinki Co., Ltd). The mixture was kneaded with 20 parts of water, and 450 grams of the kneaded mixture were molded to a product having a diameter of 100 mm in a cylindrical mold of 100 mm in diameter. The product was then immersed in a 20% aqueous solution of calcium nitrate for 10 minutes and dried at 50° C. for 30 minutes in a fluidized bed dryer to yield the Composition (42) of the invention.

PREPARATION EXAMPLE 43

Clay was added to a mixture consisting of 5 parts of a pesticidally active ingredient (43), 5 parts of Solvesso 200

(organic solvent manufactured by Exxon Chemical Corp.), 10 parts of white carbon, and 20 parts of sodium alginate to the total amount of 100 parts and mixed well with a chemical mixer (Model H-85: manufactured by Kokusan Enshinki Co., Ltd). While 15 parts of water were sprayed, the mixture was granulated to granules having the average diameter of 30 mm with a pan granulator. The granules were then immersed in a 20% aqueous solution of calcium nitrate for 2 hours and dried at 50° C. for 30 minutes in a fluidized bed dryer to yield the Composition (43) of the invention.

PREPARATION EXAMPLE 44

A mixture of 1.5 parts of a pesticidally active ingredient (90) and 0.3 parts of white carbon mixed with a blender was ground by a centrifugal grinder (Model ZM-1: manufactured by Nihon Seiki Manufacturing Ltd). Ten parts of sodium alginate and clay were added successively to the ground mixture to the total amount of 100 parts and mixed well with a chemical mixer (Model H-85: manufactured by Kokusan Enshinki Co., Ltd). The mixture was kneaded with 20 parts of water and granulated to granules having the average diameter of 20 mm with an extrusion granulator. The granules were then immersed in a 10% aqueous solution of calcium chloride for 60 minutes and dried at 50° C. for 30 minutes in a fluidized bed dryer to yield the Composition (44) of the invention.

PREPARATION EXAMPLE 45

A mixture of 1.5 parts of a pesticidally active ingredient (90) and 0.3 parts of white carbon mixed with a blender was ground by a centrifugal grinder (Model ZM-1: manufactured by Nihon Seiki Manufacturing Ltd). Ten parts of sodium alginate and clay were added successively to the ground mixture to the total amount of 100 parts and mixed well with a chemical mixer (Model H-85: manufactured by Kokusan Enshinki Co., Ltd). While 12 parts of water were sprayed, the mixture was granulated under blending to granules having the average diameter of 20 mm by Mechanomill (manufactured by Okada Seiko Co., Ltd). The granules were then immersed in a 10% aqueous solution of calcium chloride for 60 minutes and dried at 50° C. for 30 minutes in a fluidized bed dryer to yield the Composition (45) of the invention.

PREPARATION EXAMPLE 46

A mixture of 1.5 parts of a pesticidally active ingredient (90) and 0.3 parts of white carbon mixed with a blender was ground by a centrifugal grinder (Model ZM-1: manufactured by Nihon Seiki Manufacturing Ltd). Ten parts of sodium alginate and clay were added successively to the ground mixture to the total amount of 100 parts and mixed well with a chemical mixer (Model H-85: manufactured by Kokusan Enshinki Co., Ltd). While 10 parts of water were sprayed, the mixture was granulated to granules having the average diameter of 20 mm by a pan granulator. The granules were then immersed in a 10% aqueous solution of calcium chloride for 60 minutes and dried at 50° C. for 30 minutes in a fluidized bed dryer to yield the Composition (46) of the invention.

PREPARATION EXAMPLE 47

A mixture of 1.5 parts of a pesticidally active ingredient (90) and 0.3 parts of white carbon mixed with a blender was ground by a centrifugal grinder (Model ZM-1: manufactured by Nihon Seiki Manufacturing Ltd). Ten parts of sodium alginate and clay were added successively to the ground mixture to the total amount of 100 parts and mixed well with a chemical mixer (Model H-85: manufactured by Kokusan Enshinki Co., Ltd). The mixture was kneaded with 30 parts of water, and 30 grams of the kneaded mixture were molded to a product having a diameter of 20 mm in a cylindrical mold of 20 mm in diameter. The product was then immersed in a 10% aqueous solution of calcium chloride for 60 minutes and dried at 50° C. for 30 minutes in a fluidized bed dryer to yield the Composition (47) of the invention.

PREPARATION EXAMPLE 48

A mixture of 6 parts of a pesticidally active ingredient (90) and 1.2 parts of white carbon mixed with a blender was ground by a centrifugal grinder (Model ZM-1: manufactured by Nihon Seiki Manufacturing Ltd). Twenty parts of sodium alginate and fine powder of calcium carbonate were added successively to the ground mixture to the total amount of 100 parts and mixed well with a chemical mixer (Model H-85: manufactured by Kokusan Enshinki Co., Ltd). The mixture was kneaded with 20 parts of water and granulated to granules having the average diameter of 30 mm with an extrusion granulator. The granules were then immersed in a 10% aqueous solution of calcium chloride for 60 minutes and dried at 50° C. for 30 minutes in a fluidized bed dryer to yield the Composition (48) of the invention.

PREPARATION EXAMPLE 49

A mixture of 12 parts of a pesticidally active ingredient (90) and 2.4 parts of white carbon mixed with a blender was ground by a centrifugal grinder (Model ZM-1: manufactured by Nihon Seiki Manufacturing Ltd). Twenty parts of sodium alginate and fine powder of calcium carbonate were added successively to the ground mixture to the total amount of 100 parts and mixed well with a chemical mixer (Model H-85: manufactured by Kokusan Enshinki Co., Ltd). While 10 parts of water were sprayed, the mixture was granulated under blending to granules having the average diameter of 40 mm by a mixing granulator. The granules were then immersed in a 10% aqueous solution of calcium chloride for 60 minutes and dried at 50° C. for 30 minutes in a fluidized bed dryer to yield the Composition (49) of the invention.

PREPARATION EXAMPLE 50

A mixture of 24 parts of a pesticidally active ingredient (90) and 4.8 parts of white carbon mixed with a blender was ground by a centrifugal grinder (Model ZM-1: manufactured by Nihon Seiki Manufacturing Ltd). Forty parts of sodium alginate and fine powder of calcium carbonate were added successively to the ground mixture to the total amount of 100 parts and mixed well with a chemical mixer (Model H-85: manufactured by Kokusan Enshinki Co., Ltd). While 30 parts of water were sprayed, the mixture was granulated to granules having the average diameter of 50 mm by a pan granulator. The granules were then immersed in a 10% aqueous solution of calcium chloride for 10 minutes and dried at 50° C. for 30 minutes in a fluidized bed dryer to yield the Composition (50) of the invention.

PREPARATION EXAMPLE 51

A mixture of 48 parts of a pesticidally active ingredient (90) and 9.6 parts of white carbon mixed with a blender was ground by a centrifugal grinder (Model ZM-1: manufactured by Nihon Seiki Manufacturing Ltd). Forty parts of sodium alginate and fine powder of calcium carbonate were added successively to the ground mixture to the total amount of 100 parts and mixed well with a chemical mixer (Model H-85: manufactured by Kokusan Enshinki Co., Ltd). The mixture was kneaded with 30 parts of water, and 60 grams of the kneaded mixture were molded to a product having a diameter of 60 mm in a cylindrical mold of 60 mm in diameter. The product was then immersed in a 10% aqueous solution of calcium chloride for 100 minutes and dried at 50° C. for 30 minutes in a fluidized bed dryer to yield the Composition (51) of the invention.

PREPARATION EXAMPLE 52

Clay was added to a mixture consisting of 5 parts of a pesticidally active ingredient (60), 5 parts of isodecyl adipate, 10 parts of white carbon, and 10 parts of sodium alginate to the total amount of 100 parts and mixed well with a chemical mixer (Model H-85: manufactured by Kokusan Enshinki Co., Ltd). The mixture was kneaded with 20 parts of water and granulated to granules having the average diameter of 30 mm with an extrusion granulator. The granules thus obtained were then treated with 20 parts of a 20% aqueous solution of calcium nitrate by spraying, and dried at 50° C. for 30 minutes in a fluidized bed dryer to yield the Composition (52) of the invention.

PREPARATION EXAMPLE 53

Clay was added to a mixture consisting of 5 parts of a pesticidally active ingredient (60), 5 parts of isodecyl adipate, 10 parts of white carbon, and 30 parts of sodium alginate to the total amount of 100 parts and mixed well with a chemical mixer (Model H-85: manufactured by Kokusan Enshinki Co., Ltd). While 15 parts of water were sprayed, the mixture was granulated under blending to granules having the average diameter of 30 mm by an blending granulator. The granules thus obtained were then treated with 20 parts of a 20% aqueous solution of calcium nitrate by spraying thereon, and dried at 50° C. for 30 minutes in a fluidized bed dryer to yield the Composition (53) of the invention.

PREPARATION EXAMPLE 54

Clay was added to a mixture consisting of 5 parts of a pesticidally active ingredient (60), 5 parts of white carbon, and 50 parts of sodium alginate to the total amount of 100 parts and mixed well with a chemical mixer (Model H-85: manufactured by Kokusan Enshinki Co., Ltd). The mixture was kneaded with 25 parts of water, and 100 grams of the kneaded mixture were molded to a product having a diameter of 80 mm with a rectangular prism mold. The product thus obtained was then immersed in a 10% aqueous solution of calcium chloride for 60 minutes and dried at 50° C. for 2 hours in a fluidized bed dryer to yield the Composition (54) of the invention.

PREPARATION EXAMPLE 55

A mixture of 1.5 parts of a pesticidally active ingredient (90) and 0.3 part of white carbon mixed with a blender was ground by a centrifugal grinder (Model ZM-1: manufactured by Nihon Seiki Manufacturing Ltd). Twenty parts of sodium alginate and clay were added successively to the ground mixture to the total amount of 100 parts and mixed well with a chemical mixer (Model H-85: manufactured by Kokusan Enshinki Co., Ltd). The mixture was kneaded with 30 parts of water, and 30 grams of the kneaded mixture were molded to a product having a diameter of 30 mm with a cylindrical mold. The product thus obtained was then immersed in a 10% aqueous solution of calcium chloride for 5 hours and dried at 50° C. for 5 hours in a fluidized bed dryer to yield the Composition (55) of the invention.

PREPARATION EXAMPLE 56

A mixture of 1.5 parts of a pesticidally active ingredient (90) and 0.3 parts of white carbon mixed with a blender was ground by a centrifugal grinder (Model ZM-1: manufactured by Nihon Seiki Manufacturing Ltd). Twenty parts of sodium alginate and clay were added successively to the ground mixture to the total amount of 100 parts and mixed well with a chemical mixer (Model H-85: manufactured by Kokusan Enshinki Co., Ltd). The mixture was kneaded with 30 parts of water, and 45 grams of the kneaded mixture were molded to a product having a diameter of 45 mm with a cylindrical mold. The product thus obtained was then immersed in a 10% aqueous solution of calcium chloride for 20 hours and dried at 50° C. for 24 hours in a fluidized bed dryer to yield the Composition (56) of the invention.

PREPARATION EXAMPLE 57

A mixture of 1.5 parts of a pesticidally active ingredient (90) and 0.3 parts of white carbon mixed with a blender was ground by a centrifugal grinder (Model ZM-1: manufactured by Nihon Seiki Manufacturing Ltd). Twenty parts of sodium alginate and clay were added successively to the ground mixture to the total amount of 100 parts and mixed well with a chemical mixer (Model H-85: manufactured by Kokusan Enshinki Co., Ltd). The mixture was kneaded with 30 parts of water, and 20 grams of the kneaded mixture were molded to a product having a diameter of 30 mm with a cylindrical mold. The product thus obtained was then immersed in a 10% aqueous solution of calcium chloride for 20 hours and dried at 50° C. for 24 hours in a fluidized bed dryer to yield the Composition (57) of the invention.

PREPARATION EXAMPLE 58

Twelve parts of a pesticidally active ingredient (90) were mixed with 2 parts of white carbon and ground by a centrifugal grinder (Model ZM-1: manufactured by Nihon Seiki Manufacturing Ltd). Ten parts of sodium alginate, 10 parts of Bentonite Fuji (manufactured by HOJUNYOKO), and clay were added successively to the ground mixture to the total amount of 100 parts and mixed well with a blender. The mixture was kneaded with 20 parts of water by a chemical mixer (Model H-85: manufactured by Kokusan Enshinki Co., Ltd) and granulated to granules having the average diameter of 1.0 mm with an extrusion granulator. After the granules were dried at 50° C. for 1 hour, those of 0.8 through 1.2 mm in diameter were separated with a sieve. The sieved granules were immersed in a 20% aqueous solution of calcium nitrate for 10 minutes and subsequently dried again to yield the granular Pesticidal Composition (58) of the invention.

Continuous granulation with an extrusion granulator gave cylindrical granules having favorably smooth surface with high efficiency.

PREPARATION EXAMPLE 59

Five parts of a pesticidally active ingredient (117) were mixed with 1 part of white carbon and ground by a centrifugal grinder. Thirty parts of sodium alginate, 3 parts of Bentonite Fuji, and fine powder of calcium carbonate were added successively to the ground mixture to the total amount of 100 parts and mixed well with a blender. The mixture was kneaded with 25 parts of water by a chemical mixer and granulated to granules having the average diameter of 1.0 mm with an extrusion granulator. After the granules were dried at 50° C. for 1 hour, those of 0.8 through 1.2 mm in diameter were separated with a sieve. The sieved granules were immersed in a 20% aqueous solution of calcium chloride for 60 minutes and subsequently dried to yield the granular Pesticidal Composition (59) of the invention.

Continuous granulation with an extrusion granulator gave cylindrical granules having favorably smooth surface with high efficiency.

PREPARATION EXAMPLE 60

Five parts of a pesticidally active ingredient (117) were mixed with 1 part of white carbon and ground by a centrifugal grinder. Thirty parts of sodium alginate, 30 parts of Bentonite Fuji, and fine powder of calcium carbonate were added successively to the ground mixture to the total amount of 100 parts and mixed well with a blender. The mixture was kneaded with 25 parts of water by a chemical mixer and granulated to granules having the average diameter of 0.8 mm with an extrusion granulator. After the granules were dried at 50° C. for 1 hour, those of 0.5 through 1.0 mm in diameter were separated with a sieve. The sieved granules were immersed in a 20% aqueous solution of calcium chloride for 60 minutes and subsequently dried again to yield the granular Pesticidal Composition (60) of the invention.

Continuous granulation with an extrusion granulator gave cylindrical granules having favorably smooth surface with high efficiency.

PREPARATION EXAMPLE 61

Five parts of a pesticidally active ingredient (117) were mixed with 1 part of white carbon and ground by a centrifugal grinder. Thirty parts of sodium alginate, 5 parts of Bentonite Fuji, and clay were added successively to the ground mixture to the total amount of 100 parts and mixed well with a blender. The mixture was kneaded with 25 parts of water by a chemical mixer and granulated to granules having the average diameter of 1.0 mm with an extrusion granulator. After the granules were dried at 50° C. for 1 hour, those of 0.8 through 1.2 mm in diameter were separated with a sieve. The sieved granules were immersed in a 10% aqueous solution of calcium chloride for 30 minutes and subsequently dried again to yield the granular Pesticidal Composition (61) of the invention.

Continuous granulation with an extrusion granulator gave cylindrical granules having favorably smooth surface with high efficiency.

PREPARATION EXAMPLE 62

Five parts of a pesticidally active ingredient (117) were mixed with 1 part of white carbon and ground by a centrifugal grinder. Thirty parts of sodium alginate, 20 parts of Bentonite Fuji, and clay were added successively to the ground mixture to the total amount of 100 parts and mixed well with a blender. The mixture was kneaded with 25 parts of water by a chemical mixer and granulated to granules having the average diameter of 0.8 mm with an extrusion granulator. After the granules were dried at 50° C. for 1 hour, those of 0.5 through 1.0 mm in diameter were separated with a sieve. The sieved granules were immersed in a 10% aqueous solution of calcium chloride for 30 minutes and subsequently dried again to yield the granular Pesticidal Composition (62) of the invention.

Continuous granulation with an extrusion granulator gave cylindrical granules having favorably smooth surface with high efficiency.

PREPARATION EXAMPLE 63

Five parts of a pesticidally active ingredient (117) were mixed with 1 part of white carbon and ground by a centrifugal grinder. Five parts of sodium alginate, 3 parts of Bentonite Fuji, and clay were added successively to the ground mixture to the total amount of 100 parts and mixed well with a blender. The mixture was kneaded with 20 parts of water by a chemical mixer and granulated to granules having the average diameter of 0.9 mm with an extrusion granulator. After the granules were dried at 50° C. for 30 minutes, those of 0.7 through 1.4 mm in diameter were separated with a sieve. The sieved granules were immersed in a 10% aqueous solution of calcium chloride for 10 minutes and subsequently dried again to yield the granular Pesticidal Composition (63) of the invention.

Continuous granulation with an extrusion granulator gave cylindrical granules having favorably smooth surface with high efficiency.

PREPARATION EXAMPLE 64

The granular Pesticidal Composition (64) of the invention was prepared in the same manner as Preparation Example 63 except that 30 parts of Bentonite Fuji were used instead of 3 parts of the same.

Continuous granulation with an extrusion granulator gave cylindrical granules having favorably smooth surface with high efficiency.

PREPARATION EXAMPLE 65

Four parts of a pesticidally active ingredient (117) were mixed with 0.8 part of white carbon and ground by a centrifugal grinder. Ten parts of sodium alginate, 10 parts of Bentonite Fuji, and clay were added successively to the ground mixture to the total amount of 100 parts and mixed well with a blender. The mixture was kneaded with 20 parts of water by a chemical mixer and granulated to granules having the average diameter of 0.9 mm with an extrusion granulator. After the granules were dried at 50° C. for 30 minutes, those of 0.7 through 1.4 mm in diameter were separated with a sieve. The sieved granules were immersed in a 10% aqueous solution of calcium chloride for 30 minutes and subsequently dried again to yield the granular Pesticidal Composition (65) of the invention.

Continuous granulation with an extrusion granulator gave cylindrical granules of the pesticide composition having favorably smooth surface with high efficiency.

PREPARATION EXAMPLE 66

Three parts of a pesticidally active ingredient (43) were mixed with 3 parts of white carbon, 10 parts of sodium alginate, and 20 parts of Bentonite Hodaka (manufactured by HOJUNYOKO). Clay was subsequently added to the mixture to the total amount of 100 parts and mixed well with a blender. The mixture was kneaded with 17 parts of water by a chemical mixer and granulated to granules having the average diameter of 0.7 mm with an extrusion granulator. After the granules were dried at 50° C. for 30 minutes, those of 0.5 through 1.0 mm in diameter were separated with a sieve. The sieved granules were immersed in a 10% aqueous

PREPARATION EXAMPLE 66 (continued)

solution of calcium chloride for 10 minutes and dried again to yield the granular Pesticidal Composition (66) of the invention.

Continuous granulation with an extrusion granulator gave cylindrical granules having favorably smooth surface with high efficiency.

PREPARATION EXAMPLE 67

A solution prepared by dissolving 0.5 parts of a pesticidally active ingredient (114) in 2 parts of phenylxylylethane was mixed with 2 parts of white carbon, 20 parts of sodium alginate, and 10 parts of Kunigel V1 (manufactured by Kunimine Industries Co., Ltd). Fine powder of calcium carbonate was subsequently added to the mixture to the total amount of 100 parts and mixed well with a blender. The mixture was kneaded with 20 parts of water by a chemical mixer and granulated to granules having the average diameter of 1.5 mm with an extrusion granulator. After the granules were dried at 50° C. for 30 minutes, those of 1.0 through 2.0 mm in diameter were separated with a sieve. The sieved granules were immersed in a 10% aqueous solution of calcium chloride for 30 minutes and dried again to yield the granular Pesticidal Composition (67) of the invention.

Continuous granulation with an extrusion granulator gave cylindrical granules having favorably smooth surface with high efficiency.

PREPARATION EXAMPLE 68

A solution prepared by dissolving 0.5 part of a pesticidally active ingredient (114) in 2 parts of phenylxylylethane was mixed with 2 parts of white carbon, 2 parts of sodium dodecylbenzenesulfonate, 10 parts of sodium alginate, and 10 parts of Kunigel V1. Fine powder of calcium carbonate was subsequently added to the mixture to the total amount of 100 parts and mixed well with a blender. The mixture was kneaded with 17 parts of water by a chemical mixer and granulated to granules having the average diameter of 1.2 mm with an extrusion granulator. After the granules were dried at 50° C. for 30 minutes, those of 1.0 through 1.5 mm in diameter were separated with a sieve. The sieved granules were immersed in a 10% aqueous solution of calcium chloride for 10 minutes and dried again to yield the granular Pesticidal Composition (68) of the invention.

Continuous granulation with an extrusion granulator gave cylindrical granules having favorably smooth surface with high efficiency.

PREPARATION EXAMPLE 69

Three parts of a pesticidally active ingredient (90) were mixed with 0.6 part of white carbon and ground by a centrifugal grinder. Five parts of sodium alginate, 10 parts of Bentonite Fuji, and clay were added successively to the ground mixture to the total amount of 100 parts and mixed well with a blender. The mixture was kneaded with 17 parts of water by a chemical mixer and granulated to granules having the average diameter of 0.9 mm with an extrusion granulator. After the granules were dried at 50° C. for 1 hour, those of 0.7 through 1.4 mm in diameter were separated with a sieve. The sieved granules were immersed in a 20% aqueous solution of calcium nitrate for 20 minutes and subsequently dried again to yield the granular Pesticidal Composition (69) of the invention.

Continuous granulation with an extrusion granulator gave cylindrical granules having favorably smooth surface with high efficiency.

PREPARATION EXAMPLE 70

The granular Pesticidal Composition (70) of the invention was prepared in the same manner as Preparation Example 69 except that 10 parts of sodium alginate were used instead of 5 parts of the same.

Continuous granulation with an extrusion granulator gave cylindrical granules having favorably smooth surface with high efficiency.

PREPARATION EXAMPLE 71

The granular Pesticidal Composition (71) of the invention was prepared in the same manner as Preparation Example 69 except that 20 parts of sodium alginate were used instead of 5 parts of the same.

Continuous granulation with an extrusion granulator gave cylindrical granules having favorably smooth surface with high efficiency.

PREPARATION EXAMPLE 72

The granular Pesticidal Composition (72) of the invention was prepared in the same manner as Preparation Example 69 except that 1.5 parts of the pesticidally active ingredient (90), 0.3 parts of white carbon, 20 parts of sodium alginate, and 20 parts of water were used respectively in place of 3 parts, 0.6 parts, 5 parts, and 17 parts of the same.

Continuous granulation with an extrusion granulator gave cylindrical granules having favorably smooth surface with high efficiency.

PREPARATION EXAMPLE 73

Five parts of a pesticidally active ingredient (43) and 5 parts of white carbon were mixed in a mortar. Clay was subsequently added to the mixture to the total weight of 100 parts and mixed well with a blender. The mixture was then kneaded with 10 parts of ethylene-vinyl acetate copolymer emulsion in a mortar and granulated to granules having the average diameter of 1.0 mm with an extrusion granulator. The granules were dried at 50° C. for 30 minutes in a fluidized bed dryer and immersed in a 1% aqueous solution of sodium alginate for 3 minutes and then in a 20% aqueous solution of calcium chloride for 10 minutes. After the immersed granules were dried again at 50° C. for 30 minutes, those of 0.5 through 1.5 mm in diameter were separated with a sieve to yield the Composition (73) of the invention.

PREPARATION EXAMPLE 74

Clay was added to a mixture consisting of 5 parts of a pesticidally active ingredient (43), 5 parts of white carbon, and 3 parts of isopropyl acid phosphate to the total amount of 100 parts and mixed well with a chemical mixer (Model H-85: manufactured by Kokusan Enshinki Co., Ltd). The mixture was kneaded with 10 parts of a 10% aqueous solution of Gohsenol NL-05 (polyvinyl alcohol manufactured by Nippon Synthetic Chemical Industry Co., Ltd) and granulated to granules having the average diameter of 1.0 mm with an extrusion granulator. The granules were once dried at 50° C. for 30 minutes in a fluidized bed dryer. Ten parts of a 0.5% aqueous solution of sodium alginate were sprayed onto the dried granules under blending with a mixer, and the granules were subsequently immersed in a 20% aqueous solution of calcium chloride for 10 minutes.

After the immersed granules were dried again at 50° C. for 30 minutes, those of 0.5 through 1.5 mm in diameter were separated with a sieve to yield the Composition (74) of the invention.

PREPARATION EXAMPLE 75

Clay was added to a mixture consisting of 5 parts of a pesticidally active ingredient (43), 5 parts of white carbon, 3 parts of epoxidized soybean oil, and 1 part of sodium dodec ylbenzenesulfonate to the total amount of 100 parts and mixed well with a chemical mixer (Model H-85: manufactured by Kokusan Enshinki Co., Ltd). The mixture was kneaded with 10 parts of ethylene-vinyl acetate copolymer emulsion and granulated to granules having the average diameter of 1.0 mm with an extrusion granulator. The granules were once dried at 50° C. for 30 minutes in a fluidized bed dryer. Ten parts of a 0.5% aqueous solution of sodium alginate were sprayed onto the dried granules under blending with a mixer, and then 10 parts of a 20% aqueous solution of calcium chloride were sprayed onto the granules under blending with a mixer. After the immersed granules were dried again at 50° C. for 30 minutes, those of 0.5 through 1.5 mm in diameter were separated with a sieve to yield the Composition (75) of the invention.

PREPARATION EXAMPLE 76

Twenty parts of a pesticidally active ingredient (148) were mixed with 5 parts of white carbon and ground by a centrifugal grinder (Model ZM-1: manufactured by Nihon Seiki Manufacturing Ltd). Two parts of sodium dodecylbenzenesulfonate and clay were added successively to the ground mixture to the total amount of 100 parts and mixed well with a blender. While 10 parts of a 2% ethanol solution of ethyl cellulose were sprayed, the mixture was tumbled and granulated to granules with a pan granulator. The granules were once dried at 40° C. for 30 minutes in a fluidized bed dryer. Ten parts of a 0.2% aqueous solution of sodium alginate were sprayed onto the dried granules under blending with a mixer and then 10 parts of a 20% aqueous solution of calcium nitrate were sprayed onto the granules under blending with a mixer. After the immersed granules were dried again at 50° C. for 30 minutes, those of 0.5 through 1.0 mm in diameter were separated with a sieve to yield the Composition (76) of the invention.

PREPARATION EXAMPLE 77

Ten parts of a pesticidally active ingredient (148) were mixed with 2 parts of white carbon and ground by a centrifugal grinder (Model ZM-1: manufactured by Nihon Seiki Manufacturing Ltd). Five parts of sodium dodecyl-benzenesulfonate and calcium carbonate were added successively to the ground mixture to the total amount of 100 parts and mixed well with a blender. While 10 parts of ethylene-vinyl acetate copolymer emulsion were sprayed, the mixture was tumbled and granulated to granules with a pan granulator. The granules were dried at 50° C. for 30 minutes in a fluidized bed dryer and immersed in a 0.5% aqueous solution of sodium alginate for 5 minutes and then in a 20% aqueous solution of calcium nitrate for 10 minutes. After the immersed granules were dried again at 50° C. for 30 minutes, those of 0.3 through 0.8 mm in diameter were separated with a sieve to yield the Composition (77) of the invention.

PREPARATION EXAMPLE 78

Six parts of a pesticidally active ingredient (117) were mixed with 1.2 parts of white carbon and ground by a centrifugal grinder (Model ZM-1: manufactured by Nihon Seiki Manufacturing Ltd). Clay was added to the ground mixture to the total amount of 100 parts and mixed well with a blender. The mixture was kneaded with 20 parts of a 10% aqueous solution of Gohsenol NL-05 (polyvinyl alcohol manufactured by The Nippon Synthetic Chemical Industry Co., Ltd) with a chemical mixer (Model H-85: manufactured by Kokusan Enshinki Co., Ltd) and granulated to granules having the average diameter of 0.7 mm with an extrusion granulator. The granules were once dried at 50° C. for 30 minutes in a fluidized bed dryer. Ten parts of a 0.5% aqueous solution of sodium alginate were sprayed onto the dried granules under blending with a mixer, and the granules were subsequently immersed in a 20% aqueous solution of calcium nitrate for 5 minutes. After the immersed granules were dried again at 50° C. for 30 minutes, those of 0.5 through 1.0 mm in diameter were separated with a sieve to yield the Composition (78) of the invention.

PREPARATION EXAMPLE 79

Six parts of a pesticidally active ingredient (117) were mixed with 1.2 parts of white carbon and ground by a centrifugal grinder (Model ZM-1: manufactured by Nihon Seiki Manufacturing Ltd). Calcium carbonate was added to the ground mixture to the total amount of 100 parts and mixed well with a blender. While 5 parts of a 2% ethanol solution of ethyl cellulose were added, the mixture was granulated to granules with a roller compactor. Under gentle blending with a mixer. 5 parts of a 2% ethanol solution of ethyl cellulose were sprayed onto the granules and 5 parts of sodium alginate were added.

After 5 parts of a 20% aqueous solution of calcium chloride were sprayed onto the granules, the granules were dried at 50° C. for 30 minutes and those of 0.7 through 1.2 mm in diameter were separated with a sieve to yield the Composition (79) of the invention.

PREPARATION EXAMPLE 80

The Composition (80) of the invention was prepared in the same manner as Preparation Example 79 except that 5 parts of calcium alginate were used instead of 5 parts of sodium alginate and that five parts of the 20% aqueous solution of calcium chloride were not sprayed.

PREPARATION EXAMPLE 81

Six parts of a pesticidally active ingredient (117) were mixed with 1.2 parts of white carbon and ground by a centrifugal grinder (Model ZM-1: manufactured by Nihon Seiki Manufacturing Ltd). Eleven parts of another pesticidally active ingredient (112), 9 parts of white carbon, and calcium carbonate were added successively to the ground mixture to the total amount of 100 parts and mixed well with a blender. While 5 parts of a 2% ethanol solution of ethyl cellulose were added, the mixture was granulated to granules with a roller compactor. Under gentle blending with a mixer, 5 parts of a 0.5% aqueous solution of sodium alginate were sprayed onto the granules. After the granules were immersed in a 20% aqueous solution of calcium chloride for 5 minutes and dried at 50° C. for 30 minutes, those of 0.5 through 1.5 mm in diameter were separated with a sieve to yield the Composition (81) of the invention.

PREPARATION EXAMPLE 82

Clay was added to a mixture consisting of 2 parts of a pesticidally active ingredient (114), 8 parts of phenylxylylethane, and 8 parts of white carbon to the total amount of 100 parts and mixed well with a blender. While 5 parts of ethylene-vinyl acetate copolymer emulsion were sprayed, the mixture was granulated to granules by Mechanomill (Model MM1-10: manufactured by Okada Seiko Co., Ltd). Under blending with a mixer, 5 parts of a 2% ethanol solution of ethyl cellulose were sprayed onto the granules, and then 5 parts of calcium alginate were added to the granules. After the granules obtained were dried at 50° C. for 30 minutes, those of 1.5 through 2.5 mm in diameter were separated with a sieve to yield the Composition (82) of the invention.

PREPARATION EXAMPLE 83

Ten parts of a pesticidally active ingredient (143) were mixed with 5 parts of white carbon and ground by a centrifugal grinder (Model ZM-1: manufactured by Nihon Seiki Manufacturing Ltd). Clay was added to the ground mixture to the total amount of 100 parts and mixed well with a blender. While 10 parts of a 10% aqueous solution of Gohsenol NL-05 (polyvinyl alcohol manufactured by The Nippon Synthetic Chemical Industry Co., Ltd) were sprayed, the mixture was granulated to granules with a fluidized bed granulator. Under blending with a mixer, 5 parts of a 0.5% aqueous solution of sodium alginate were sprayed onto the granules and the granules were immersed in a 10% aqueous solution of barium chloride for 5 minutes. After the granules obtained were dried at 50° C. for 30 minutes, those of 0.7 through 1.2 mm in diameter were separated with a sieve to yield the Composition (83) of the invention.

PREPARATION EXAMPLE 84

A mixture of 1.5 parts of a pesticidally active ingredient (90) and 0.3 parts of white carbon was ground by a centrifugal grinder (Model ZM-1: manufactured by Nihon Seiki Manufacturing Ltd). Clay was added to the ground mixture to the total amount of 100 parts and mixed well with a blender. The mixture was kneaded with 20 parts of ethylene-vinyl acetate copolymer emulsion by a chemical mixer (Model H-85: manufactured by Kokusan Enshinki Co., Ltd) and granulated to granules having the average diameter of 0.9 mm with an extrusion granulator. Under blending with a mixer, the granules were immersed in a 1% aqueous solution of sodium alginate for 5 minutes and dried at 50° C. for 30 minutes and then the granules were immersed in a 20% aqueous solution of calcium chloride for 10 minutes. After the granules were dried at 50° C. for 30 minutes, those of 0.7 through 1.2 mm in diameter were separated with a sieve to yield the Composition (84) of the invention.

PREPARATION EXAMPLE 85

The Composition (85) of the invention was prepared in the same manner as Preparation Example 84 except that 6 parts of the pesticidally active ingredient (90) and 1.2 parts of white carbon were used respectively in place of 1.5 parts and 0.3 parts of the same, 20 parts of a 10% aqueous solution of Gohsenol NL-05 (polyvinyl alcohol manufactured by Nippon Synthetic Chemical Industry Co., Ltd) in place of 20 parts of the ethylene-vinyl acetate copolymer emulsion, and a 20% aqueous solution of calcium nitrate instead of the 20% aqueous solution of calcium chloride.

PREPARATION EXAMPLE 86

A mixture of 1.5 parts of a pesticidally active ingredient (90) and 0.3 parts of white carbon was ground by a centrifugal grinder (Model ZM-1: manufactured by Nihon Seiki Manufacturing Ltd). Under blending, 5 parts of ethylene-vinyl acetate copolymer emulsion were sprayed onto silica sand. The ground mixture was added to the silica sand and granulated to granules by Mechanomill (Model MM-10: manufactured by Okada Seiko Co., Ltd). Under blending with a mixer, 5 parts of a 0.5% aqueous solution of sodium alginate and 10 parts of a 20% aqueous solution of calcium nitrate were sprayed successively onto the granules. After the granules were dried at 50° C. for 30 minutes, those of 0.5 through 1.5 mm in diameter were separated with a sieve to yield the Composition (86) of the invention.

PREPARATION EXAMPLE 87

While 99.5 parts of ISHIKAWALITE 2 (pumice manufactured by ISHIKAWALITE INDUSTRIES Co., Ltd.) were stirred with a mixer, 0.5 parts of a pesticidally active ingredient (114) heated and melted at 50° C. in a warm bath were added to the pumice to give granules. The granules thus obtained were immersed successively in a 2% aqueous solution of sodium alginate for 5 minutes and then the granules were immersed in a 10% aqueous solution of calcium chloride for 10 minutes and dried at 50° C. for 30 minutes in a fluidized bed dryer to yield the Composition (87) of the invention.

PREPARATION EXAMPLE 88

While 95 parts of AGSORB LVM-MS 12/24 (attapulgite manufactured by OIL DRI Corp.) were stirred with a mixer, 5 parts of a pesticidally active ingredient (112) were added to the attapulgite to give granules. The granules thus obtained were impregnated with 30 parts of a 1% aqueous solution of sodium alginate, which were added under blending of the granules with a mixer. The granules were then immersed in a 20% aqueous solution of calcium nitrate for 10 minutes and dried at 50° C. for 30 minutes in a fluidized bed dryer to yield the Composition (88) of the invention.

PREPARATION EXAMPLE 89

While 94 parts of AGSORB LVM-MS 8/16 (attapulgite manufactured by OIL DRI Corp.) were stirred with a mixer, 5 parts of a pesticidally active ingredient (112) and 1 part of sodium dodecylbenzenesulfonate were added to the attapulgite to give granules. The granules thus obtained were impregnated with 60 parts of a 1% aqueous solution of sodium alginate, which were added under blending of the granules with a mixer. The granules were then immersed in a 10% aqueous solution of calcium chloride for 10 minutes and dried at 50° C. for 30 minutes in a fluidized bed dryer to yield the Composition (89) of the invention.

PREPARATION EXAMPLE 90

While 98.5 parts of AGSORB LVM-NIS 10/20 (attapulgite manufactured by OIL DRI Corp.) were stirred with a mixer, 1.5 parts of a pesticidally active ingredient (90) dissolved in 30 parts of dichloromethane were added to the attapulgite and dried at 40° C. for 1 hour to give granules. The granules thus obtained were impregnated with 60 parts of a 0.5% aqueous solution of sodium alginate, which were added under blending of the granules with a mixer. The granules were then immersed in a 20% aqueous solution of calcium nitrate for 60 minutes and dried at 50° C. for 30 minutes in a fluidized bed dryer to yield the Composition (90) of the invention.

PREPARATION EXAMPLE 91

While 98.5 parts of AGSORB LVM-MS 12/24 (attapulgite manufactured by OIL DRI Corp.) were stirred with a mixer, 1.5 parts of a pesticidally active ingredient (90) dissolved in 50 parts of dichloromethane were added to the attapulgite and dried at 40° C. for 1 hour to give granules. The granules thus obtained were impregnated with 60 parts of a 1% aqueous solution of sodium alginate, which were added under blending of the granules with a mixer. After a 10% aqueous solution of calcium chloride was sprayed, the granules were dried at 50° C. for 30 minutes in a fluidized bed dryer to yield the Composition (91) of the invention.

PREPARATION EXAMPLE 92

While 94 parts of AGSORB LVM-MS 12/24 (attapulgite manufactured by OIL DRI Corp.) were stirred with a mixer, 6 parts of a pesticidally active ingredient (90) dissolved in 30 parts of dichloromethane were added to the attapulgite and dried at 40° C. for 1 hour to give granules. The granules thus obtained were immersed successively in a 3% aqueous solution of sodium alginate for 5 minutes and in a 10% aqueous solution of calcium chloride for 5 minutes and dried at 50° C. for 30 minutes in a fluidized bed dryer to yield the Composition (92) of the invention.

PREPARATION EXAMPLE 93

Five parts of a pesticidally active ingredient (117), 20 parts of dichloromethane, and 5 parts of Highsol SAS-296 (manufactured by Nippon Petrochemicals Co., Ltd.) were mixed sufficiently to a homogeneous solution. Under blending with a mixer, 90 parts of Isolite CG-1 (pumice manufactured by Isolite Insulating Products Co., Ltd.) were impregnated with the homogeneous solution and dried at 40° C. for 1 hour to give granules. The granules thus obtained were impregnated with 30 parts of a 1% aqueous solution of sodium alginate, which were added under blending of the granules with a mixer. The granules were then immersed in a 20% aqueous solution of calcium nitrate for 20 minutes and dried at 50° C. for 30 minutes in a fluidized bed dryer to yield the Composition (93) of the invention.

PREPARATION EXAMPLE 94

Five parts of a pesticidally active ingredient (117), 20 parts of dichloromethane, and 5 parts of cottonseed oil were mixed sufficiently to a homogeneous solution. Under blending with a mixer, 90 parts of Aplus (diatomaceous earth manufactured by Isolite Insulating Products Co., Ltd.) were impregnated with the homogeneous solution and dried at 40° C. for 1 hour to give granules. The granules thus obtained were impregnated with 30 parts of a 1% aqueous solution of sodium alginate, which were added under blending of the granules with a mixer. The granules were then immersed in a 10% aqueous solution of barium chloride for 20 minutes and dried at 50° C. for 30 minutes in a fluidized bed dryer to yield the Composition (94) of the invention.

PREPARATION EXAMPLE 95

One part of Tween 20 (surfactant manufactured by ICI America Corp.), 0.1 part of a pesticidally active ingredient (115), and 10 parts of dichloromethane were mixed sufficiently to a homogeneous solution. Under blending with a mixer, 98.5 parts of ISHIKAWALITE 2 (pumice manufactured by ISHIKAWALITE INDUSTRIES Co., Ltd.) were impregnated with the homogeneous solution and dried at 40° C. for 1 hour to give granules. The granules thus obtained were impregnated with 5 parts of a 1% aqueous solution of sodium alginate, which were added under blending of the granules with a mixer. After a 10% aqueous solution of calcium chloride was sprayed, the granules were dried at 50° C. for 30 minutes in a fluidized bed dryer to yield the Composition (95) of the invention.

PREPARATION EXAMPLE 96

Ninety-nine parts of Fubasami Clay A-300 (clay manufactured by Fubasami Clay Industries Co., Ltd.) and 10 parts of a 10% aqueous solution of Gohsenol NL-05 (polyvinyl alcohol manufactured by Nippon Synthetic Chemical Industry Co., Ltd.) were kneaded and granulated to granules having the average diameter of 1.0 mm with an extrusion granulator. After the granules were dried at 50° C. for 30 minutes, 95 parts of the granules were impregnated with 5 parts of a pesticidally active ingredient (112) under blending with a mixer. The granules were then immersed successively in a 1% aqueous solution of sodium alginate for 3 minutes and a 20% aqueous solution of calcium nitrate for 5 minutes and dried at 50° C. for 30 minutes in a fluidized bed dryer to yield the Composition (96) of the invention.

Exemplified preparations of conventional granular pesticide compositions are given below as references.

REFERENCE EXAMPLE 1

Three parts of a pesticidally active ingredient (90) were mixed with 0.6 parts of white carbon and ground by a centrifugal grinder (Model ZM-1: manufactured by Nihon Seiki Manufacturing Ltd). Thirty parts of bentonite, 4 parts of sodium dodecylbenzenesulfonate, and clay were added successively to the ground mixture to the total amount of 100 parts and mixed well with a blender. The mixture was kneaded with 15 parts of water by a chemical mixer (Model H-85: manufactured by Kokusan Enshinki Co., Ltd) and granulated to granules having the average diameter of 1.5 mm with an extrusion granulator. After the granules were dried at 50° C. for 1 hour, those of 1.2 through 1.8 mm in diameter were separated with a sieve to yield the Reference Composition (1).

REFERENCE EXAMPLE 2

Three parts of a pesticidally active ingredient (90) were mixed with 0.6 parts of white carbon and ground by a centrifugal grinder (Model ZM-1: manufactured by Nihon Seiki Manufacturing Ltd). Twenty parts of sodium alginate, and clay were added successively to the ground mixture to the total amount of 100 parts and mixed well with a blender. The mixture was kneaded with 20 parts of water by a chemical mixer (Model H-85: manufactured by Kokusan Enshinki Co., Ltd) and granulated to granules having the average diameter of 1.5 mm with an extrusion granulator. After the granules were dried at 50° C. for 1 hour, those of 1.2 through 1.8 mm in diameter were separated with a sieve to yield the Reference Composition (2).

REFERENCE EXAMPLE 3

A mixture of 1.5 parts of a pesticidally active ingredient (90) and 0.3 parts of white carbon was ground by a centrifugal grinder (Model ZM-1: manufactured by Nihon Seiki Manufacturing Ltd). Thirty parts of bentonite, 4 parts of sodium dodecylbenzenesulfonate, and clay were added successively to the ground mixture to the total amount of 100 parts and mixed well with a blender. The mixture was kneaded with 15 parts of water by a chemical mixer (Model H-85: manufactured by Kokusan Enshinki Co., Ltd) and granulated to yield granules of the Reference Composition (3) having the average diameter of 0.9 mm with an extrusion granulator.

REFERENCE EXAMPLE 4

Eight parts of white carbon were mixed with 10.5 parts of a pesticidally active ingredient (112). Thirty parts of bentonite, 4 parts of sodium dodecylbenzenesulfonate, and clay were added successively to the mixture to the total amount of 100 parts and mixed well with a blender. The mixture was kneaded with 20 parts of water by a chemical mixer (Model H-85: manufactured by Kokusan Enshinki Co., Ltd) and granulated to granules having the average diameter of 0.5 mm with an extrusion granulator. The granules were dried at 50° C. for 1 hour to yield the Reference Composition (4).

REFERENCE EXAMPLE 5

A mixture of 1.5 parts of a pesticidally active ingredient (90) and 0.3 parts of white carbon was ground by a centrifugal grinder (Model ZM-1: manufactured by Nihon Seiki Manufacturing Ltd). Four parts of Sorpol 5060 (surfactant manufactured by Toho Chemicals Co., Ltd.), 30 part of bentonite, and clay were added successively to the ground mixture to the total amount of 100 parts and mixed well with a chemical mixer (Model H-85: manufactured by Kokusan Enshinki Co., Ltd). The mixture was kneaded with 30 parts of water, and 45 grams of the kneaded mixture were molded to a product having a diameter of 30 mm in a cylindrical mold. The product thus obtained was dried at 50° C. for 24 hours in a fluidized bed dryer to yield the Reference Composition (5).

REFERENCE EXAMPLE 6

A mixture of 1.5 parts of a pesticidally active ingredient (90) and 0.3 parts of white carbon was ground by a centrifugal grinder (Model ZM-1: manufactured by Nihon Seiki Manufacturing Ltd). Clay was added to the ground mixture to the total amount of 100 parts and mixed well with a blender. The mixture was kneaded with 20 parts of ethylene-vinyl acetate copolymer emulsion by a chemical mixer (Model H-85: manufactured by Kokusan Enshinki Co., Ltd.) and granulated to granules having the average diameter of 0.9 mm with an extrusion granulator. The Reference Composition (6) was yielded by separating granules of 0.7 through 1.2 mm in diameter with a sieve.

REFERENCE EXAMPLE 7

While 98.5 parts of AGSORB LVM-MS 10/20 (attapulgite manufactured by OIL DRI Corp.) were stirred with a mixer, 1.5 parts of a pesticidally active ingredient (90) dissolved in 30 parts of dichloromethane were added to the attapulgite and dried at 40° C. for 1 hour to yield the Reference Composition (7).

The following tests were performed to verify the sustained release of the pesticidally active ingredient from the composition of the invention.

TEST EXAMPLE 1

One gram of each Composition of the invention or Reference Composition was gently stirred with 300 ml of 3° hardness water in a 500 ml beaker. The water temperature was set at 25±1° C. After a predetermined time period, 1 ml of each sample solution was collected on the center of the beaker and the content of the pesticidally active ingredient in the sample solution was determined by liquid chromatography. The rate of dissolution of active ingredient was determined according to the equation expressed as:

$$\text{Rate of dissolution (\%)} = \frac{\text{Content of Pesticidally Active Ingredient (mg) in 1 ml of Sample Solution} \times 300}{\text{Initial Amount of Pesticidally Active Ingredient (mg) contained in 1 g of Composition}} \times 100$$

[Equation 1]

Tables 1 through 4 show the results of the determination.

TABLE 1

| | Rate of Dissolution (%) | |
|---|---|---|
| | After 3 days | After 7 days |
| Composition (1) | 37 | 65 |
| Composition (3) | 21 | 45 |
| Composition (6) | 13 | 39 |
| Reference Composition (1) | 98 | 100 |
| Reference Composition (2) | 95 | 99 |

As shown in Table 1, the pesticidally active ingredient was mostly eluted out of the conventional granular pesticide compositions, that is, the Reference Composition (1) and the Reference Composition (2), in three days. In the composition of the invention, on the contrary, sustained release of the pesticidally active ingredient was observed and elution proceeded even after seven days or later.

TABLE 2

| | Rate of Dissolution (%) | | |
|---|---|---|---|
| | After 1 day | After 3 days | After 10 days |
| Composition (71) | 31 | 48 | 78 |

As shown in Table 2, the granular pesticide composition of the invention had effects of sustained release of the pesticidally active ingredient and elution proceeded even after ten days or later.

TABLE 3

| | Rate of Dissolution (%) | |
|---|---|---|
| | After 2 days | After 7 days |
| Composition (84) | 55 | 85 |
| Reference Composition (6) | 100 | 100 |

As shown in Table 3, the pesticidally active ingredient was mostly eluted out of the conventional granular pesticide composition, that is, the Reference Composition (6), in two days. In the composition of the invention, however, sustained release of the pesticidally active ingredient was observed and elution proceeded even after 7 days or later.

TABLE 4

| | Rate of Dissolution (%) | | |
|---|---|---|---|
| | After 3 days | After 7 days | After 14 days |
| Composition (90) | — | 56 | 72 |
| Reference Composition (7) | 95 | 100 | 100 |

As shown in Table 4, the pesticidally active ingredient was mostly eluted out of the conventional granular pesticide composition, that is, the Reference Composition (7), in three days. In the composition of the invention, however, sustained release of the pesticidally active ingredient was observed and elution proceeded even after 14 days or later.

TEST EXAMPLE 2

Each Composition obtained according to the preparation above was gently stirred with 5000 ml of tap water in a 5000 ml beaker. The water temperature was set at 25±1° C. After a predetermined time period, 1 ml of each sample solution was collected on the center of the beaker and the content of the pesticidally active ingredient in the sample solution was determined by liquid chromatography. The rate of dissolution of active ingredient was determined according-to the equation expressed as:

$$\text{Rate of Elution (\%)} = \frac{\text{Content of Pesticidally Active Ingredient (mg) in 1 ml of Sample Solution} \times 5000}{\text{Initial Amount of Pesticidally Active Ingredient (mg) contained in 1 g of Composition}} \times 100 \quad [\text{Equation 2}]$$

Table 5 shows the results of the determination.

TABLE 5

| | Rate of Dissolution (%) | | |
|---|---|---|---|
| | After 2 days | After 10 days | After 20 days |
| Composition (54) | 2 | 28 | 83 |
| Composition (56) | 2 | 26 | 78 |

As shown in Table 5, the compositions of the invention having relatively large particle diameter attained longer sustained release of the pesticidally active ingredient.

TEST EXAMPLE 3

Rice plants (*Oriza Sativa* L.) planted in 1/10000-are wagner pots were cultivated in a glass greenhouse kept at 23 through 28° C. The young rice plants at 6-leaf stage were treated respectively with the Composition (22) of the invention and the Reference Composition (3) at the concentration of 4 kg/10 ares. After 20-day cultivation and 40-day cultivation, strains of rice blight (Pellicularia sasaki) were inoculated on the roots of the rice plants. After seven-day cultivation under conditions of high humidity, the strain-control effects were examined.

The disease control were determined by substituting the maximum lesion measured into the following equation:

$$\text{Disease Control (\%)} = \frac{\text{Maximum Lesion in untreated plant} - \text{Maximum Lesion in treated plant}}{\text{Maximum Lesion in untreated plant}} \times 100 \quad [\text{Equation 3}]$$

Table 6 shows the results of the determination.

TABLE 6

| | Disease Control (%) | |
|---|---|---|
| | After 20 days | After 40 days |
| Composition (22) | 77 | 86 |
| Reference Composition (3) | 85 | 56 |

As shown in Table 6, while the Reference Composition (3) had a significantly low disease control after 40 days, the Composition of the invention still kept a high efficacy even after 40 days.

TEST EXAMPLE 4

Seeds of bulrush (*Scirpus junc.* v. *ohwianus*) were sowed in 1/5000-are wagner pots and kept in a glass greenhouse. Prior to germination, the seeds were treated with the Compositions (9) and (65) of the invention at the concentration of 300 grams/are and the wagner pots were kept. After a predetermined time period, the wagner pots were observed for numerical evaluation of herbicidal effects: 0 (No Effect) through 100 (Completely Dead).

Table 7 shows the results of the evaluation.

TABLE 7

| | Herbicidal Effects | | |
|---|---|---|---|
| | After 14 days | After 28 days | After 35 days |
| Composition (9) | — | 93 | 90 |
| Composition (65) | 93 | 93 | 90 |

As shown in Table 7, the pesticide composition of the invention exerted excellent herbicidal effects over a long time period.

TEST EXAMPLE 5

Young rice plants with 2-leaf stages (*Oriza Sativa* L.) were planted in 1/5000-are wagner pots and treated respectively with the Composition (24) of the invention and the Reference Composition (4) at the concentration of 100 g/are. The wagner pots thus treated were kept in a greenhouse. After 28 days, phytotoxicity of the compositions on the rice plants were numerically evaluated: 0 (No Damage) through 10 (Completely Dead).

Table 8 shows the results of the evaluation.

TABLE 8

| | After 28 days |
|---|---|
| Composition (24) | 1 |
| Reference Composition (4) | 2.5 |

TEST EXAMPLE 6

The Composition (55) of the invention and the Reference Composition (5) were respectively placed in vinyl chloride pipes (inner diameter: 7 cm), through which tap water ran at the flow of 2,000 ml/minute. After a predetermined time period, the water flow was cut and the compositions remaining in the pipes were collected, and the pesticidally active ingredient of each composition was measured by liquid chromatography. The residual rate was determined according to the equation expressed as:

$$\text{Residual Rate (\%)} = \frac{\text{Content of Pesticidally Active Ingredient (mg) in Composition Collected}}{\text{Initial Amount of Pesticidally Active Ingredient (mg) contained in 1 g of Composition}} \times 100.$$

Table 9 shows the results of the determination.

TABLE 9

|  | Residual Rate (%) | |
| --- | --- | --- |
|  | After 2 days | After 7 days |
| Composition (55) | 62 | 37 |
| Reference Composition (5) | 0.2 | 0 |

As shown in Table 9, while the pesticidally active ingredient was released rapidly from the Reference Composition (5), the Cvomposition (55) of the invention having relatively large particle diameter preferably controlled the release of the pesticidally active ingredient in the flow of water. Some amount of the pesticidally active ingredient remained in water even after seven days.

What is claimed is:

1. A pesticidal composition containing a water-insoluble alginate, which is prepared by treating a solid composition containing (a) a pesticidally active ingredient which is a pest-controlling active ingredient or a plant growth-regulating active ingredient and (b) an alginic acid or a water-soluble alginate with an aqueous solution containing a divalent or polyvalent cation which can convert said alginic acid or water-soluble alginate into a water-insoluble alginate.

2. The pesticidal composition according to claim 1, wherein said water-insoluble alginate has a three dimensional matrix structure.

3. The pesticidal composition according to claim 1, wherein said solid composition further contains bentonite.

4. The pesticidal composition according to claim 2, wherein said solid composition further contains bentonite.

5. The pesticidal composition according to claim 1, wherein said solid composition contains a pesticidally active ingredient, bentonite and an alginic acid or a water-soluble alginate, and is prepared by the method of extrusion granulation.

6. The pesticidal composition containing a water-insoluble alginate, wherein a solid substance containing a pesticidally active ingredient which is a pest-controlling active ingredient or a plant growth-regulating active ingredient is coated with a water-insoluble alginate.

7. The pesticidal composition according to claim 1. wherein said solid composition is prepared by coating a solid substance containing a pesticidally active ingredient with an alginic acid or a water-soluble alginate.

8. A pesticidal composition containing a water-insoluble alginate, which is prepared by coating a solid substance containing a pesticidally active ingredient which is a pest-controlling active ingredient or a plant growth-regulating active ingredient with a water-insoluble alginate.

9. A pesticidal composition containing a water-insoluble alginate, wherein a water-insoluble alginate is impregnated into a solid substance containing a pesticidally active ingredient which is a pest-controlling active ingredient or a plant growth-regulating active ingredient.

10. A pesticidal composition containing a water-insoluble alginate, wherein a water-insoluble alginate is impregnated into a solid substance containing a pesticidally active ingredient which is a pest-controlling active ingredient or a plant growth-regulating active ingredient and an absorbent carrier.

11. The pesticidal composition according to claim 1, wherein said solid composition is prepared by impregnating an alginic acid or a water-soluble alginate into a solid substance containing a pesticidally active ingredient and an absorbent carrier.

12. The pesticidal composition according to claim 1, wherein said cation is a calcium cation.

13. A method for preparing a pesticidal composition, which comprises treating a solid composition containing (a) a pesticidally active ingredient which is a pest-controlling active ingredient or a plant growth-regulating active ingredient and (b) an alginic acid or a water-soluble alginate with an aqueous solution containing a divalent or polyvalent cation which can convert said alginic acid or water-soluble alginate into a water-insoluble alginate.

14. The method according to claim 13, wherein an alginic acid or a water-soluble alginate contained in said solid composition has a three-dimensional matrix structure.

15. The method according to claim 13, wherein said solid composition contains a pesticidally active ingredient, bentonite and an alginic acid or a water-soluble alginate, and is prepared by the method of extrusion granulation.

16. The method according to claim 13, wherein said solid composition is prepared by coating a solid substance containing a pesticidally active ingredient with an alginic acid or a water-soluble alginate.

17. A method for preparing a pesticidal composition, which comprises coating a solid composition containing a pesticidally active ingredient which is a pest-controlling active ingredient or a plant growth-regulating active ingredient with a water-insoluble alginate.

18. The method according to claim 13, wherein said solid composition is prepared by impregnating an alginic acid or a water-soluble alginate into a solid substance containing a pesticidally active ingredient and an absorbing carrier.

19. The method according to claim 13, wherein the solid composition is immersed in the aqueous solution.

20. A method for controlling pests or regulating the growth of plants, which comprises applying a pesticidally effective amount of a pesticidal composition according to claim 1 to an area where the pests live or will live, or the plants grow or will grow.

21. The method according to claim 20, wherein the area is an aqueous environment.

22. The method according to claim 20, wherein the area is a water stream.

* * * * *